US 11,862,311 B2

(12) United States Patent
Feldschuh

(10) Patent No.: US 11,862,311 B2
(45) Date of Patent: *Jan. 2, 2024

(54) BLOOD VOLUME ANALYZER WITH GUIDANCE

(71) Applicant: DAXOR CORP., New York, NY (US)

(72) Inventor: Jonathan Feldschuh, Jackson Heights, NY (US)

(73) Assignee: DAXOR CORP., New York, NY (US)

( * ) Notice: Subject to any disclaimer, the term of this patent is extended or adjusted under 35 U.S.C. 154(b) by 750 days.

This patent is subject to a terminal disclaimer.

(21) Appl. No.: 16/667,945

(22) Filed: Oct. 30, 2019

(65) Prior Publication Data

US 2020/0132676 A1 Apr. 30, 2020

Related U.S. Application Data

(60) Provisional application No. 62/753,174, filed on Oct. 31, 2018.

(51) Int. Cl.

| G16H 20/00 | (2018.01) |
|---|---|
| G16H 10/20 | (2018.01) |
| A61B 5/145 | (2006.01) |
| G16H 20/17 | (2018.01) |
| G01N 33/50 | (2006.01) |
| A61M 5/14 | (2006.01) |

(52) U.S. Cl.
CPC ......... *G16H 20/00* (2018.01); *A61B 5/14535* (2013.01); *G16H 10/20* (2018.01); *G16H 20/17* (2018.01); *A61M 5/14* (2013.01); *G01N 33/50* (2013.01)

(58) Field of Classification Search
None
See application file for complete search history.

(56) References Cited

U.S. PATENT DOCUMENTS

| 5,024,231 A | 6/1991 | Feldschuh et al. |
|---|---|---|
| 9,002,656 B2 | 4/2015 | Feldschuh et al. |
| 9,002,657 B2 | 4/2015 | Feldschuh et al. |
| 11,204,356 B2 | 12/2021 | Feldschuh et al. |
| 2008/0195023 A1 | 8/2008 | Feldschuh |
| 2014/0100868 A1* | 4/2014 | Condurso ............ G16H 20/10 705/2 |
| 2018/0217168 A1 | 8/2018 | Feldschuh et al. |
| 2020/0132668 A1 | 4/2020 | Feldschuh et al. |
| 2020/0132677 A1 | 4/2020 | Feldschuh et al. |

(Continued)

FOREIGN PATENT DOCUMENTS

| WO | 2021/222575 A1 | 11/2021 |
|---|---|---|
| WO | 2021/222594 A1 | 11/2021 |

OTHER PUBLICATIONS

Ertl AC, Diedrich A, Raj SR. Techniques used for the determination of blood volume. Am J Med Sci. Jul. 2007;334(1):32-6. doi: 10.1097/MAJ.0b013e318063c6d1. PMID: 17630589. (Year: 2007).*

(Continued)

*Primary Examiner* — Devin C Hein
(74) *Attorney, Agent, or Firm* — Amster, Rothstein & Ebenstein LLP

(57) ABSTRACT

Systems and methods are provided for analyzing blood of a living being, and for presenting guidance for medical treatment.

20 Claims, 26 Drawing Sheets

(56) References Cited

U.S. PATENT DOCUMENTS

2020/0297259 A1    9/2020   Feldschuh

OTHER PUBLICATIONS

Daxor, http://www.daxor.com/pdfs/bva100-brochure.pdf (Year: 2014).*
Hoff R, Rinkel G, Verweij B, Algra A, Kalkman C. Blood volume measurement to guide fluid therapy after aneurysmal subarachnoid hemorrhage: a prospective controlled study. Stroke. Jul. 2009;40(7):2575-7. doi: 10.1161/STROKEAHA.108.538116. Epub May 7, 2009. PMID: 19423854. (Year: 2009).*
Mitchell T Saltzberg, Blood Volume Analysis Coupled with Ultra-filtration in the Management of Congestive Heart Failure—Guided Therapy to Achieve Euvolemia, US Cardiology 2010;7(1):72-5 https://doi.org/10.15420/usc.2010.7.1.72 (Year: 2010).*

* cited by examiner

Daxor Blood Volume Analysis Report

| Patient Name | Analyzed On | DOB | Gender | Height | Weight | Dev. from Ideal Wt. |
|---|---|---|---|---|---|---|
| *** | 2015*** | 1943*** (71 yo) | Male | 170.18 cm | 78.02 kg | +15.8% |

| | Result | Flag | Ref. Range | Notes |
|---|---|---|---|---|
| Deviations from Ideal | | | | |
| • Total Blood Volume (% dev) | -19.4% | *L | ±11% | Moderate Hypovolemia |
| • Red Cell Volume (% dev) | -49.8% | *L | ±11% | Extreme Anemia |
| • Plasma Volume (% dev) | +1.4% | | ±10% | |
| Volumes | | | | |
| • Total Blood Volume (ml) | 3910 ml | *L | 4320-5390 ml | deficit = 940 ml |
| • Red Cell Volume (ml) | 990 ml | *L | 1750-2180 ml | deficit = 980 ml |
| • Plasma Volume (ml) | 2930 ml | | 2600-3170 ml | |
| Hct | 28 | *L | 40.5-49 | VERY LOW |

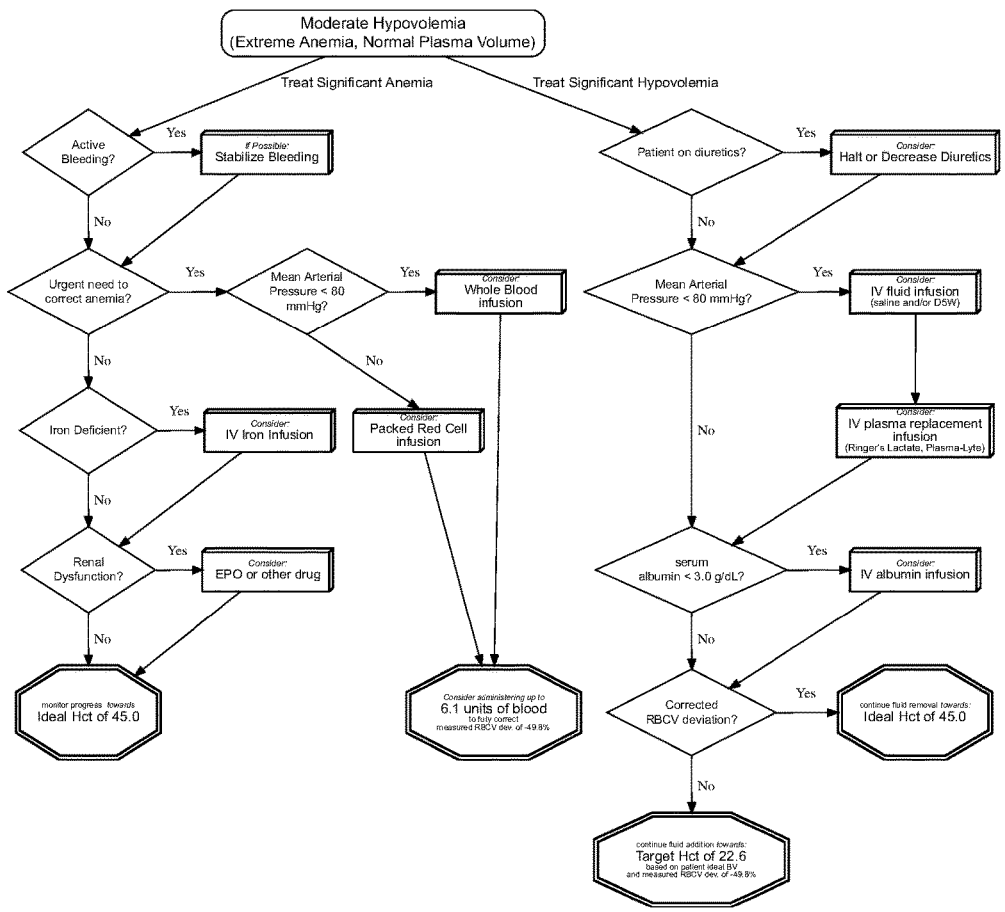

| Location | Hospital ID | Accession | Referring MD | Analyst | CC | Injectate Lot |
|---|---|---|---|---|---|---|
| *** | *** | *** | *** | *** | *** | *** |

FIGURE 1

Daxor Blood Volume Analysis Report

| Patient Name | Analyzed On | DOB | Gender | Height | Weight | Dev. from Ideal Wt. |
|---|---|---|---|---|---|---|
| *** | 2015*** | 1936*** (79 yo) | Female | 158 cm | 59.8 kg | +11.5% |

|  | Result | Flag | Ref. Range | Notes |
|---|---|---|---|---|
| Deviations from Ideal |  |  |  |  |
| • Total Blood Volume (% dev) | -25.3% | *L | ±11% | Severe Hypovolemia |
| • Red Cell Volume (% dev) | -15.9% | *L | ±11% | Mild Anemia |
| • Plasma Volume (% dev) | -30.7% | *L | ±10% | Severe Plasma Volume Deficit |
| Volumes |  |  |  |  |
| • Total Blood Volume (ml) | 2840 ml | *L | 3390-4230 ml | deficit = 960 ml |
| • Red Cell Volume (ml) | 1150 ml | *L | 1220-1520 ml | deficit = 220 ml |
| • Plasma Volume (ml) | 1690 ml | *L | 2190-2680 ml | deficit = 750 ml |
| Hct | 45.1 | *H | 36-44 | HIGH |

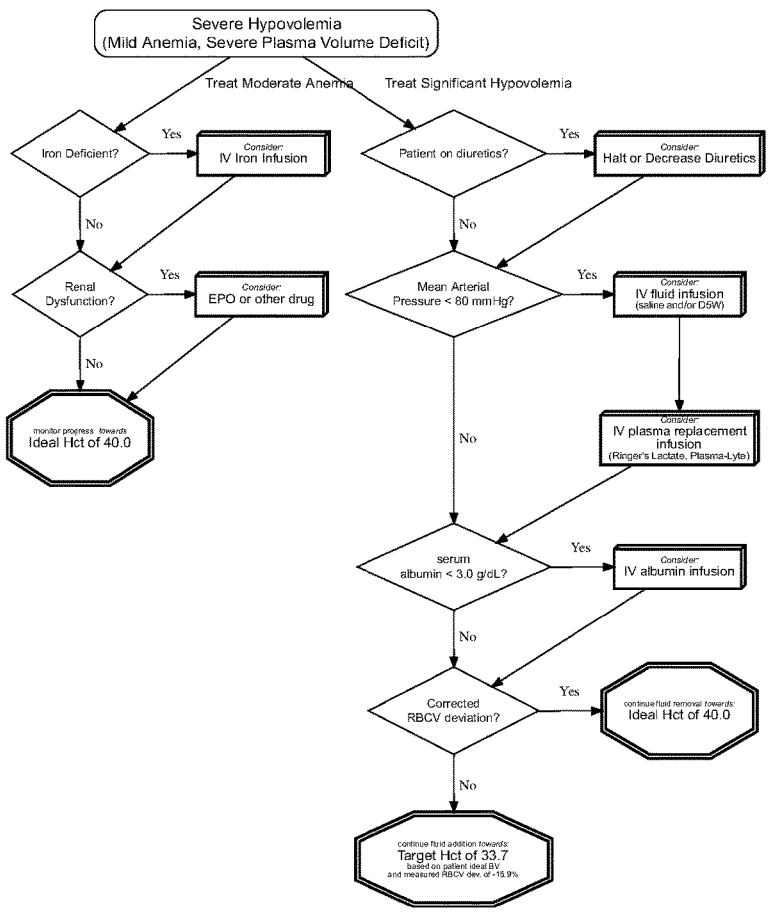

| Location | Hospital ID | Accession | Referring MD | Analyst | CC | Injectate Lot |
|---|---|---|---|---|---|---|
| *** | *** | *** | *** | *** | *** |  |

FIGURE 2

Daxor Blood Volume Analysis Report

| Patient Name | Analyzed On | DOB | Gender | Height | Weight | Dev. from Ideal Wt. |
|---|---|---|---|---|---|---|
| *** | 2008*** | 1950*** (58 yo) | Female | 159 cm | 71 kg | +30.9% |

| | Result | Flag | Ref. Range | Notes |
|---|---|---|---|---|
| Deviations from Ideal | | | | |
| • Total Blood Volume (% dev) | -21.5% | *L | ±11% | Moderate Hypovolemia |
| • Red Cell Volume (% dev) | -7.5% | | ±11% | |
| • Plasma Volume (% dev) | -29.4% | *L | ±10% | Moderate Plasma Volume Deficit |
| Volumes | | | | |
| • Total Blood Volume (ml) | 3210 ml | *L | 3640-4550 ml | deficit = 880 ml |
| • Red Cell Volume (ml) | 1360 ml | | 1310-1640 ml | |
| • Plasma Volume (ml) | 1850 ml | *L | 2360-2880 ml | deficit = 770 ml |
| Hct | 47.2 | *H | 36-44 | VERY HIGH |

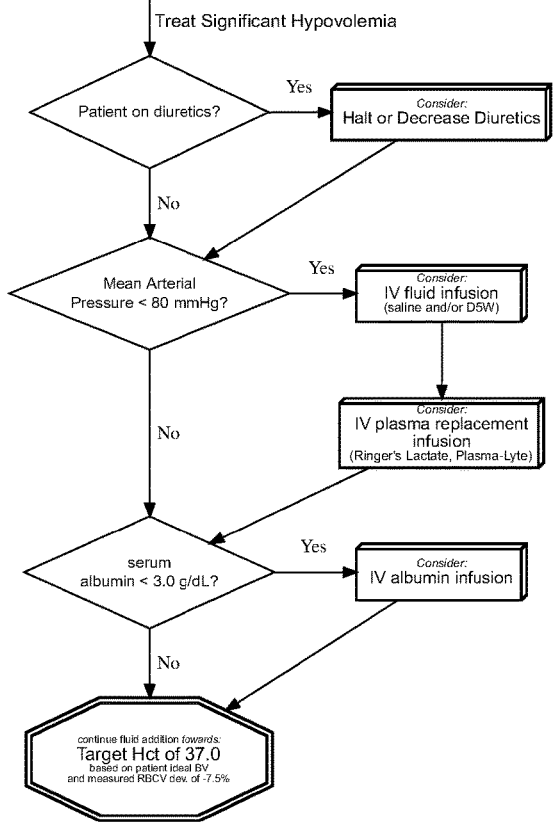

| Location | Hospital ID | Accession | Referring MD | Analyst | CC | Injectate Lot |
|---|---|---|---|---|---|---|
| *** | *** | *** | *** | *** | *** | *** |

FIGURE 3

Daxor Blood Volume Analysis Report

| Patient Name | Analyzed On | DOB | Gender | Height | Weight | Dev. from Ideal Wt. |
|---|---|---|---|---|---|---|
| *** | 2004*** | NA***NA (NA yo) | Female | 149.86 cm | 73.03 kg | +49.1% |

| | Result | Flag | Ref. Range | Notes |
|---|---|---|---|---|
| Deviations from Ideal | | | | |
| • Total Blood Volume (% dev) | -34.6% | *L | ±11% | Extreme Hypovolemia |
| • Red Cell Volume (% dev) | +12.8% | *H | ±11% | Mild Red Cell Excess |
| • Plasma Volume (% dev) | -61.3% | *L | ±10% | Extreme Plasma Volume Deficit |
| Volumes | | | | |
| • Total Blood Volume (ml) | 2580 ml | *L | 3510-4380 ml | deficit = 1370 ml |
| • Red Cell Volume (ml) | 1600 ml | *H | 1270-1580 ml | excess = 180 ml |
| • Plasma Volume (ml) | 980 ml | *L | 2270-2780 ml | deficit = 1550 ml |
| Hct | 69 | *H | 36-44 | VERY HIGH |

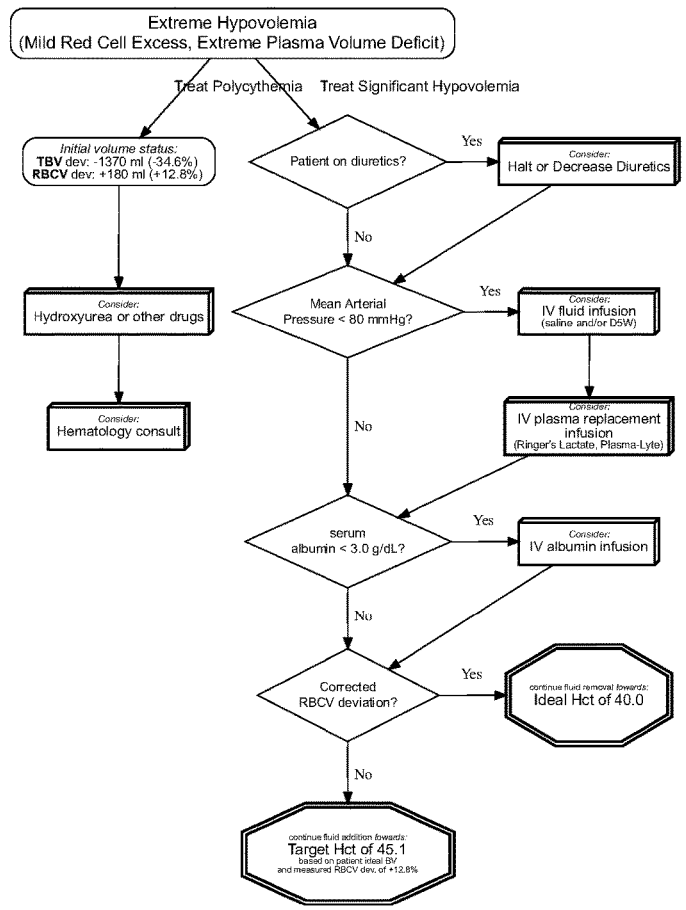

| Location | Hospital ID | Accession | Referring MD | Analyst | CC | Injectate Lot |
|---|---|---|---|---|---|---|
| *** | *** | *** | *** | *** | *** | *** |

FIGURE 4

Daxor Blood Volume Analysis Report

| Patient Name | Analyzed On | DOB | Gender | Height | Weight | Dev. from Ideal Wt. |
|---|---|---|---|---|---|---|
| *** | 2012*** | 1919*** (94 yo) | Female | 154.94 cm | 60.78 kg | +17.5% |

| | Result | Flag | Ref. Range | Notes |
|---|---|---|---|---|
| Deviations from Ideal | | | | |
| • Total Blood Volume (% dev) | -13.6% | *L | ±11% | Mild Hypovolemia |
| • Red Cell Volume (% dev) | -25.5% | *L | ±11% | Severe Anemia |
| • Plasma Volume (% dev) | -6.8% | | ±10% | |
| Volumes | | | | |
| • Total Blood Volume (ml) | 3240 ml | *L | 3340-4160 ml | deficit = 510 ml |
| • Red Cell Volume (ml) | 1010 ml | *L | 1200-1500 ml | deficit = 340 ml |
| • Plasma Volume (ml) | 2230 ml | | 2160-2640 ml | |
| Hct | 34.5 | *L | 36-44 | LOW |

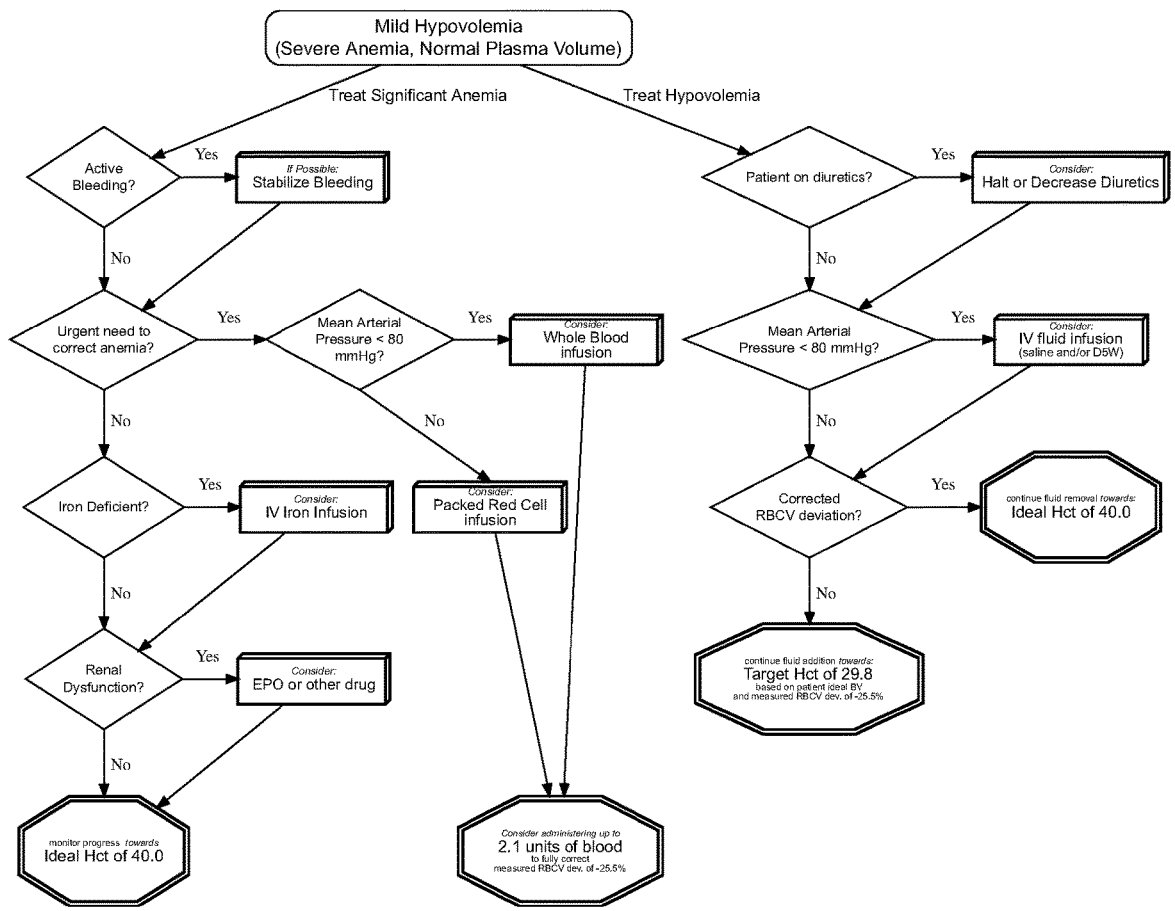

| Location | Hospital ID | Accession | Referring MD | Analyst | CC | Injectate Lot |
|---|---|---|---|---|---|---|
| *** | *** | *** | *** | *** | *** | *** |

FIGURE 5

Daxor Blood Volume Analysis Report

| Patient Name | Analyzed On | DOB | Gender | Height | Weight | Dev. from Ideal Wt. |
|---|---|---|---|---|---|---|
| *** | 2013*** | 1981*** (32 yo) | Male | 205.74 cm | 98.43 kg | -2.4% |

| | Result | Flag | Ref. Range | Notes |
|---|---|---|---|---|
| Deviations from Ideal | | | | |
| • Total Blood Volume (% dev) | -12.1% | *L | ±11% | Mild Hypovolemia |
| • Red Cell Volume (% dev) | -14.5% | *L | ±11% | Mild Anemia |
| • Plasma Volume (% dev) | -10.5% | *L | ±10% | Mild Plasma Volume Deficit |
| Volumes | | | | |
| • Total Blood Volume (ml) | 6160 ml | *L | 6240-7780 ml | deficit = 850 ml |
| • Red Cell Volume (ml) | 2430 ml | *L | 2530-3150 ml | deficit = 410 ml |
| • Plasma Volume (ml) | 3730 ml | *L | 3750-4580 ml | deficit = 440 ml |
| Hct | 43.8 | | 40.5-49 | normal |

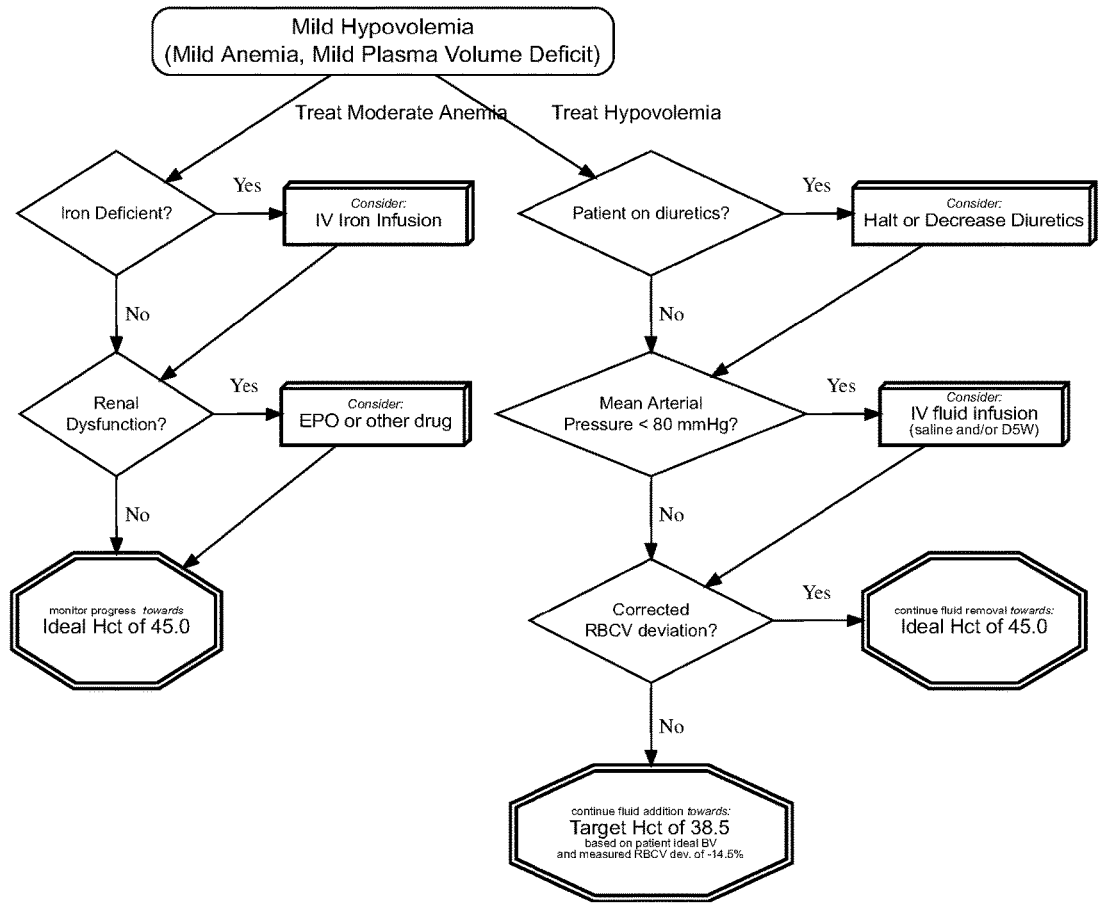

| Location | Hospital ID | Accession | Referring MD | Analyst | CC | Injectate Lot |
|---|---|---|---|---|---|---|
| *** | *** | *** | *** | *** | *** | *** |

FIGURE 6

Daxor Blood Volume Analysis Report

| Patient Name | Analyzed On | DOB | Gender | Height | Weight | Dev. from Ideal Wt. |
|---|---|---|---|---|---|---|
| *** | 2016*** | 1963*** (53 yo) | Female | 167.64 cm | 56.7 kg | -6.4% |

| | Result | Flag | Ref. Range | Notes |
|---|---|---|---|---|
| Deviations from Ideal | | | | |
| • Total Blood Volume (% dev) | -11.6% | *L | ±11% | Mild Hypovolemia |
| • Red Cell Volume (% dev) | -8.3% | | ±11% | Mild Anemia |
| • Plasma Volume (% dev) | -13.4% | *L | ±10% | Mild Plasma Volume Deficit |
| Volumes | | | | |
| • Total Blood Volume (ml) | 3680 ml | *L | 3710-4620 ml | deficit = 480 ml |
| • Red Cell Volume (ml) | 1380 ml | | 1340-1670 ml | deficit = 120 ml |
| • Plasma Volume (ml) | 2310 ml | *L | 2400-2930 ml | deficit = 360 ml |
| Hct | 41.5 | | 36-44 | normal |

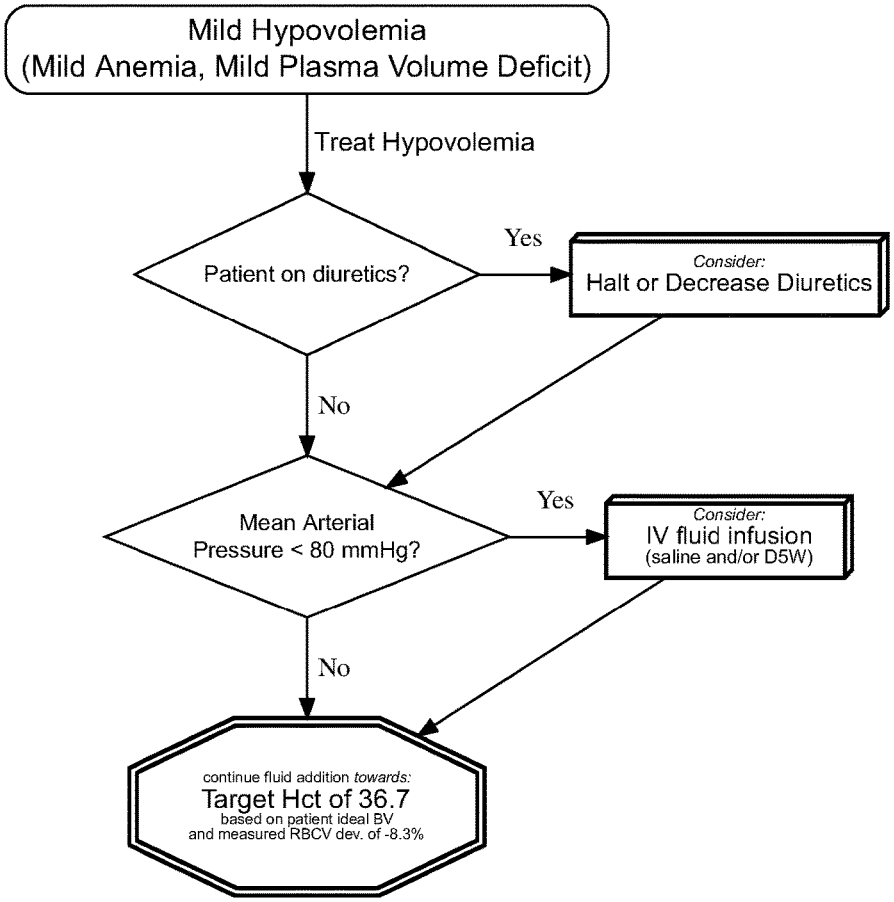

| Location | Hospital ID | Accession | Referring MD | Analyst | CC | Injectate Lot |
|---|---|---|---|---|---|---|
| *** | *** | *** | *** | *** | *** | *** |

FIGURE 7

Daxor Blood Volume Analysis Report

| Patient Name | Analyzed On | DOB | Gender | Height | Weight | Dev. from Ideal Wt. |
|---|---|---|---|---|---|---|
| *** | 2006*** | 1916*** (90 yo) | Female | 149.86 cm | 44.51 kg | -9.1% |

| | Result | Flag | Ref. Range | Notes |
|---|---|---|---|---|
| Deviations from Ideal | | | | |
| • Total Blood Volume (% dev) | -13.3% | *L | ±11% | Mild Hypovolemia |
| • Red Cell Volume (% dev) | +13.8% | *H | ±11% | Mild Red Cell Excess |
| • Plasma Volume (% dev) | -28.6% | *L | ±10% | Moderate Plasma Volume Deficit |
| Volumes | | | | |
| • Total Blood Volume (ml) | 2900 ml | *L | 2980-3710 ml | deficit = 450 ml |
| • Red Cell Volume (ml) | 1370 ml | *H | 1070-1340 ml | excess = 170 ml |
| • Plasma Volume (ml) | 1530 ml | *L | 1930-2350 ml | deficit = 610 ml |
| Hct | 52.5 | *H | 36-44 | VERY HIGH |

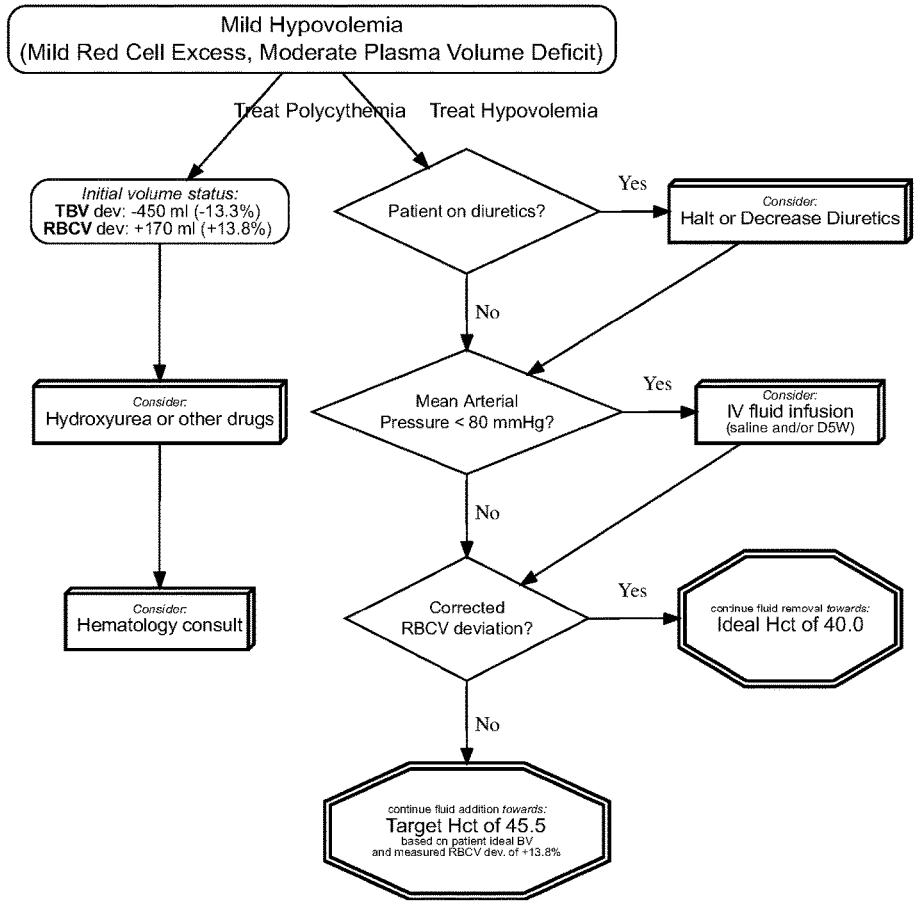

| Location | Hospital ID | Accession | Referring MD | Analyst | CC | Injectate Lot |
|---|---|---|---|---|---|---|
| *** | *** | *** | *** | *** | *** | *** |

FIGURE 8

Daxor Blood Volume Analysis Report

| Patient Name | Analyzed On | DOB | Gender | Height | Weight | Dev. from Ideal Wt. |
|---|---|---|---|---|---|---|
| *** | 2016*** | 1944*** (72 yo) | Female | 168.91 cm | 96.16 kg | +56.5% |

|  | Result | Flag | Ref. Range | Notes |
|---|---|---|---|---|
| Deviations from Ideal | | | | |
| • Total Blood Volume (% dev) | -6.6% |  | ±11% | |
| • Red Cell Volume (% dev) | -21.5% | *L | ±11% | Moderate Anemia |
| • Plasma Volume (% dev) | +1.8% |  | ±10% | |
| Volumes | | | | |
| • Total Blood Volume (ml) | 4750 ml |  | 4520-5640 ml | |
| • Red Cell Volume (ml) | 1440 ml | *L | 1630-2030 ml | deficit = 390 ml |
| • Plasma Volume (ml) | 3310 ml |  | 2930-3580 ml | |
| Hct | 33.6 | *L | 36-44 | VERY LOW |

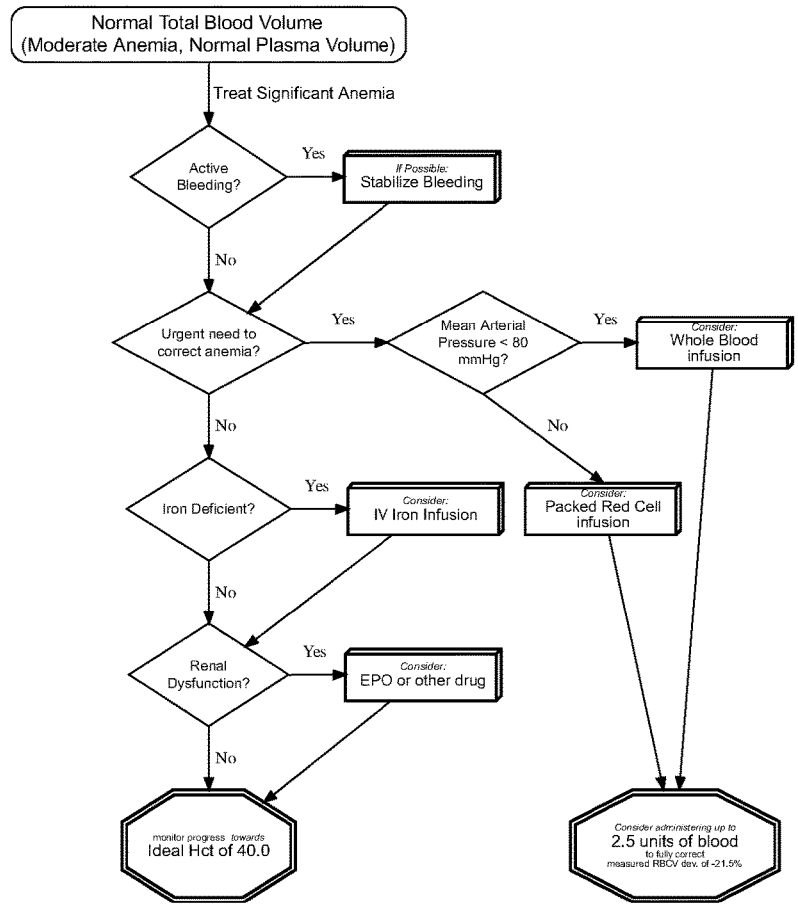

| Location | Hospital ID | Accession | Referring MD | Analyst | CC | Injectate Lot |
|---|---|---|---|---|---|---|
| *** | *** | *** | *** | *** | *** | *** |

FIGURE 9

Daxor Blood Volume Analysis Report

| Patient Name | Analyzed On | DOB | Gender | Height | Weight | Dev. from Ideal Wt. |
|---|---|---|---|---|---|---|
| *** | 2014*** | 1995*** (20 yo) | Female | 165.1 cm | 64.41 kg | +9.7% |

| | Result | Flag | Ref. Range | Notes |
|---|---|---|---|---|
| Deviations from Ideal | | | | |
| • Total Blood Volume (% dev) | -6.2% | | ±11% | |
| • Red Cell Volume (% dev) | -14.6% | *L | ±11% | Mild Anemia |
| • Plasma Volume (% dev) | -1.4% | | ±10% | |
| Volumes | | | | |
| • Total Blood Volume (ml) | 3910 ml | | 3710-4620 ml | |
| • Red Cell Volume (ml) | 1280 ml | *L | 1340-1660 ml | deficit = 220 ml |
| • Plasma Volume (ml) | 2620 ml | | 2400-2930 ml | |
| Hct | 36.4 | | 36-44 | moderately low |

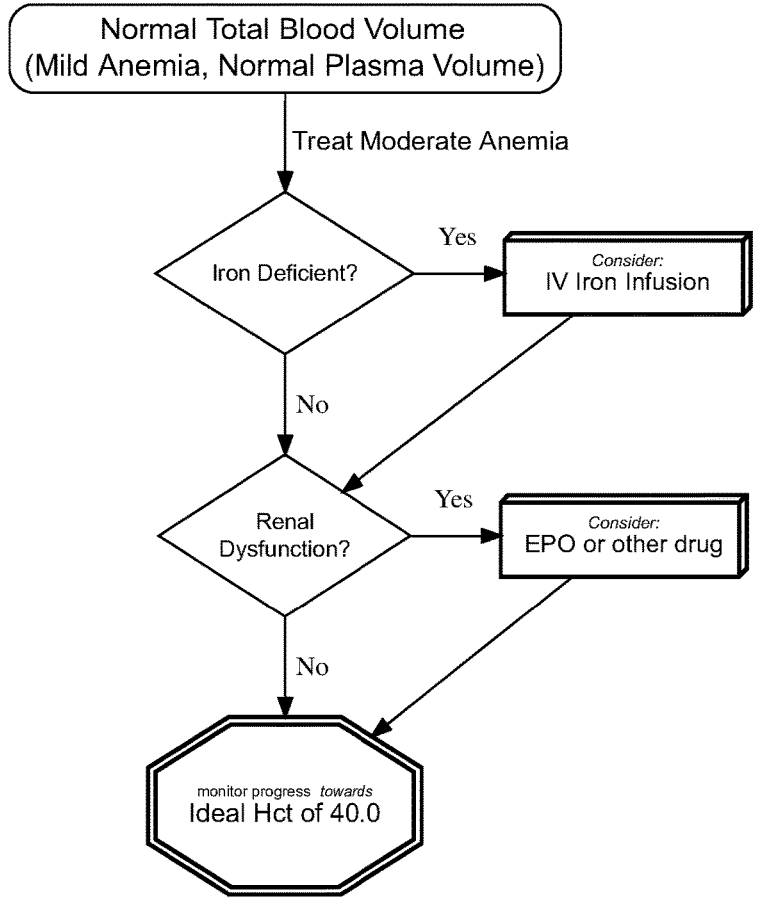

| Location | Hospital ID | Accession | Referring MD | Analyst | CC | Injectate Lot |
|---|---|---|---|---|---|---|
| *** | *** | *** | *** | *** | *** | |

FIGURE 10

Daxor Blood Volume Analysis Report

| Patient Name | Analyzed On | DOB | Gender | Height | Weight | Dev. from Ideal Wt. |
|---|---|---|---|---|---|---|
| *** | 2017*** | 1968*** (49 yo) | Female | 162.56 cm | 55.79 kg | -2.0% |

| | Result | Flag | Ref. Range | Notes |
|---|---|---|---|---|
| Deviations from Ideal | | | | |
| • Total Blood Volume (% dev) | -1.2% | | ±11% | |
| • Red Cell Volume (% dev) | -3.9% | | ±11% | |
| • Plasma Volume (% dev) | +0.3% | | ±10% | |
| Volumes | | | | |
| • Total Blood Volume (ml) | 3910 ml | | 3530-4400 ml | |
| • Red Cell Volume (ml) | 1370 ml | | 1270-1580 ml | |
| • Plasma Volume (ml) | 2540 ml | | 2280-2790 ml | |
| Hct | 38.9 | | 36-44 | normal |

Normal

| Location | Hospital ID | Accession | Referring MD | Analyst | CC | Injectate Lot |
|---|---|---|---|---|---|---|
| *** | *** | *** | *** | *** | *** | |

FIGURE 11

Daxor Blood Volume Analysis Report

| Patient Name | Analyzed On | DOB | Gender | Height | Weight | Dev. from Ideal Wt. |
|---|---|---|---|---|---|---|
| *** | 2017*** | 1939*** (78 yo) | Male | 182.88 cm | 119.29 kg | +53.7% |

|  | Result | Flag | Ref. Range | Notes |
|---|---|---|---|---|
| Deviations from Ideal | | | | |
| • Total Blood Volume (% dev) | +14.6% | *H | ±11% | Mild Hypervolemia |
| • Red Cell Volume (% dev) | -40.2% | *L | ±11% | Extreme Anemia |
| • Plasma Volume (% dev) | +51.9% | *H | ±10% | Extreme Plasma Volume Excess |
| Volumes | | | | |
| • Total Blood Volume (ml) | 7280 ml | *H | 5660-7060 ml | excess = 920 ml |
| • Red Cell Volume (ml) | 1540 ml | *L | 2290-2860 ml | deficit = 1040 ml |
| • Plasma Volume (ml) | 5740 ml | *H | 3400-4160 ml | excess = 1960 ml |
| Hct | | 23.5 | *L | 40.5-49 | VERY LOW |

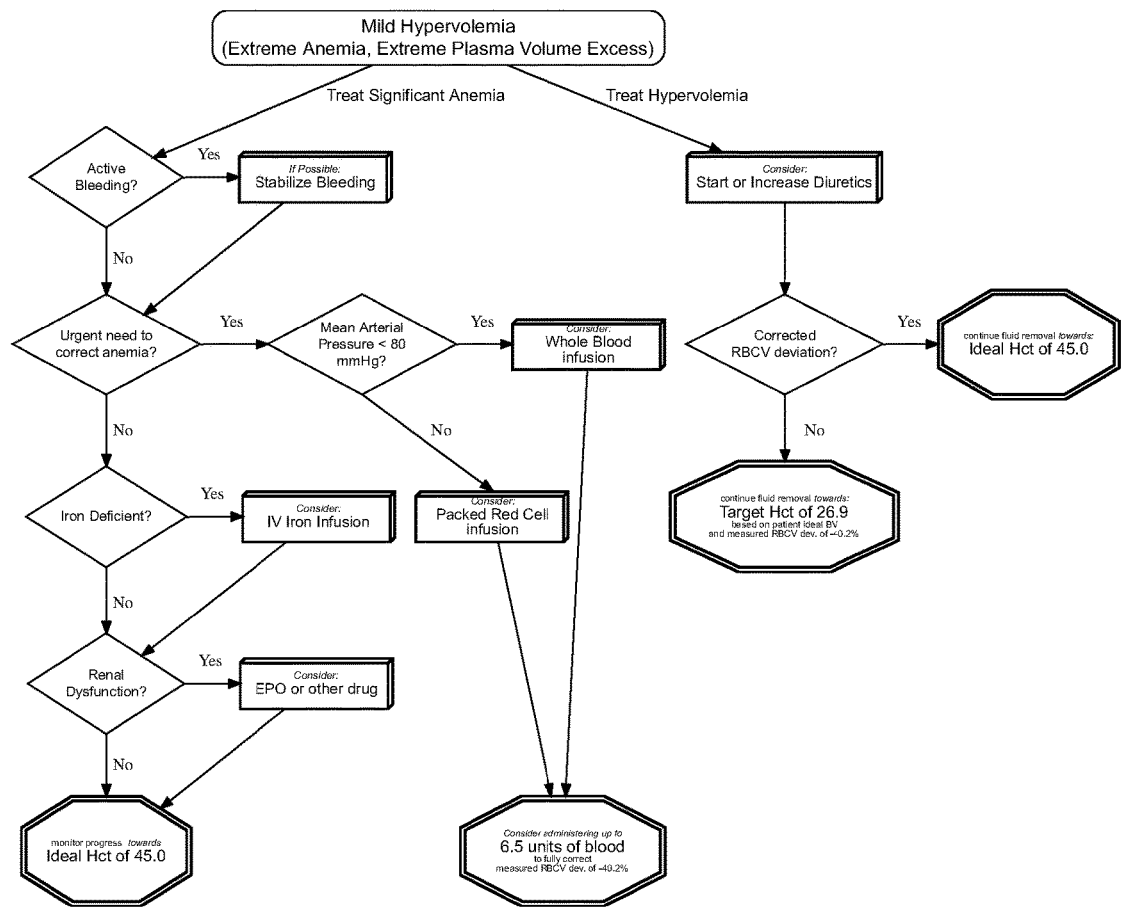

| Location | Hospital ID | Accession | Referring MD | Analyst | CC | Injectate Lot |
|---|---|---|---|---|---|---|
| *** | *** | *** | *** | *** | *** | |

FIGURE 13

Daxor Blood Volume Analysis Report

| Patient Name | Analyzed On | DOB | Gender | Height | Weight | Dev. from Ideal Wt. |
|---|---|---|---|---|---|---|
| *** | 2013*** | 1953*** (60 yo) | Female | 154.94 cm | 74.39 kg | +43.9% |

| | Result | Flag | Ref. Range | Notes |
|---|---|---|---|---|
| Deviations from Ideal | | | | |
| • Total Blood Volume (% dev) | +14.2% | *H | ±11% | Mild Hypervolemia |
| • Red Cell Volume (% dev) | -10.1% | | ±11% | Mild Anemia |
| • Plasma Volume (% dev) | +27.9% | *H | ±10% | Moderate Plasma Volume Excess |
| Volumes | | | | |
| • Total Blood Volume (ml) | 4660 ml | *H | 3630-4530 ml | excess = 580 ml |
| • Red Cell Volume (ml) | 1320 ml | | 1310-1630 ml | deficit = 150 ml |
| • Plasma Volume (ml) | 3340 ml | *H | 2350-2870 ml | excess = 730 ml |
| Hct | 31.5 | *L | 36-44 | VERY LOW |

Mild Hypervolemia
(Mild Anemia, Moderate Plasma Volume Excess)

↓ Treat Hypervolemia

*Consider:*
Start or Increase Diuretics

↓ continue fluid removal *towards:*
Target Hct of 36.0
based on patient ideal BV
and measured RBCV dev. of -10.1%

| Location | Hospital ID | Accession | Referring MD | Analyst | CC | Injectate Lot |
|---|---|---|---|---|---|---|
| *** | *** | *** | *** | *** | *** | |

FIGURE 14

Daxor Blood Volume Analysis Report

| Patient Name | Analyzed On | DOB | Gender | Height | Weight | Dev. from Ideal Wt. |
|---|---|---|---|---|---|---|
| *** | 2013*** | 1937*** (76 yo) | Female | 162.56 cm | 63.5 kg | +11.6% |

| | Result | Flag | Ref. Range | Notes |
|---|---|---|---|---|
| Deviations from Ideal | | | | |
| • Total Blood Volume (% dev) | +14.7% | *H | ±11% | Mild Hypervolemia |
| • Red Cell Volume (% dev) | -1.1% | | ±11% | |
| • Plasma Volume (% dev) | +23.5% | *H | ±10% | Moderate Plasma Volume Excess |
| Volumes | | | | |
| • Total Blood Volume (ml) | 4630 ml | *H | 3600-4480 ml | excess = 590 ml |
| • Red Cell Volume (ml) | 1440 ml | | 1300-1620 ml | |
| • Plasma Volume (ml) | 3190 ml | *H | 2330-2840 ml | excess = 610 ml |
| Hct | 34.5 | *L | 36-44 | LOW |

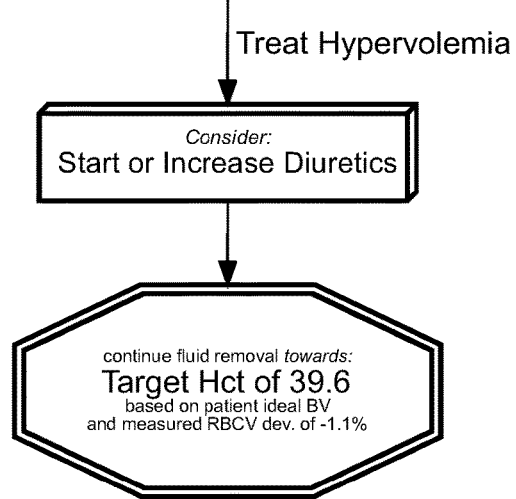

Mild Hypervolemia
(Normal Red Cell Volume, Moderate Plasma Volume Excess)

Treat Hypervolemia

*Consider:*
Start or Increase Diuretics continue fluid removal *towards:*
Target Hct of 39.6
based on patient ideal BV
and measured RBCV dev. of -1.1%

| Location | Hospital ID | Accession | Referring MD | Analyst | CC | Injectate Lot |
|---|---|---|---|---|---|---|
| *** | *** | *** | *** | *** | *** | |

FIGURE 15

Daxor Blood Volume Analysis Report

| Patient Name | Analyzed On | DOB | Gender | Height | Weight | Dev. from Ideal Wt. |
|---|---|---|---|---|---|---|
| *** | 2017*** | 1960*** (58 yo) | Male | 177.8 cm | 129.73 kg | +77.1% |

| | Result | Flag | Ref. Range | Notes |
|---|---|---|---|---|
| Deviations from Ideal | | | | |
| • Total Blood Volume (% dev) | +12.1% | *H | ±11% | Mild Hypervolemia |
| • Red Cell Volume (% dev) | +31.3% | *H | ±11% | Severe Red Cell Excess |
| • Plasma Volume (% dev) | -1.0% | | ±10% | |
| Volumes | | | | |
| • Total Blood Volume (ml) | 7270 ml | *H | 5770-7200 ml | excess = 780 ml |
| • Red Cell Volume (ml) | 3450 ml | *H | 2340-2920 ml | excess = 820 ml |
| • Plasma Volume (ml) | 3820 ml | | 3470-4240 ml | |
| Hct | 52.7 | *H | 40.5-49 | VERY HIGH |

Mild Hypervolemia
(Severe Red Cell Excess, Normal Plasma Volume)

Treat Polycythemia

*Initial volume status:*
TBV dev: +780 ml (+12.1%)
RBCV dev: +820 ml (+31.3%)

Consider:
Therapeutic Erythropheresis?

Yes → Consider removal of up to
780 ml of packed red cells
to reach patient Ideal TBV No → Consider:
Hydroxyurea or other drugs Consider:
Hematology consult

*Post-erythropheresis volume status:*
TBV dev: +0 ml (+0.1%)
RBCV dev: +40 ml (+1.6%)

| Location | Hospital ID | Accession | Referring MD | Analyst | CC | Injectate Lot |
|---|---|---|---|---|---|---|
| *** | *** | *** | *** | *** | *** | |

FIGURE 16

Daxor Blood Volume Analysis Report

| Patient Name | Analyzed On | DOB | Gender | Height | Weight | Dev. from Ideal Wt. |
|---|---|---|---|---|---|---|
| *** | 2016*** | 1945*** (71 yo) | Male | 182.88 cm | 60.33 kg | -22.3% |

| | Result | Flag | Ref. Range | Notes |
|---|---|---|---|---|
| Deviations from Ideal | | | | |
| • Total Blood Volume (% dev) | +26.8% | *H | ±11% | Severe Hypervolemia |
| • Red Cell Volume (% dev) | -19.2% | *L | ±11% | Moderate Anemia |
| • Plasma Volume (% dev) | +58.1% | *H | ±10% | Extreme Plasma Volume Excess |
| Volumes | | | | |
| • Total Blood Volume (ml) | 6500 ml | *H | 4560-5690 ml | excess = 1370 ml |
| • Red Cell Volume (ml) | 1680 ml | *L | 1850-2310 ml | deficit = 400 ml |
| • Plasma Volume (ml) | 4820 ml | *H | 2740-3350 ml | excess = 1770 ml |
| Hct | 28.7 | *L | 40.5-49 | VERY LOW |

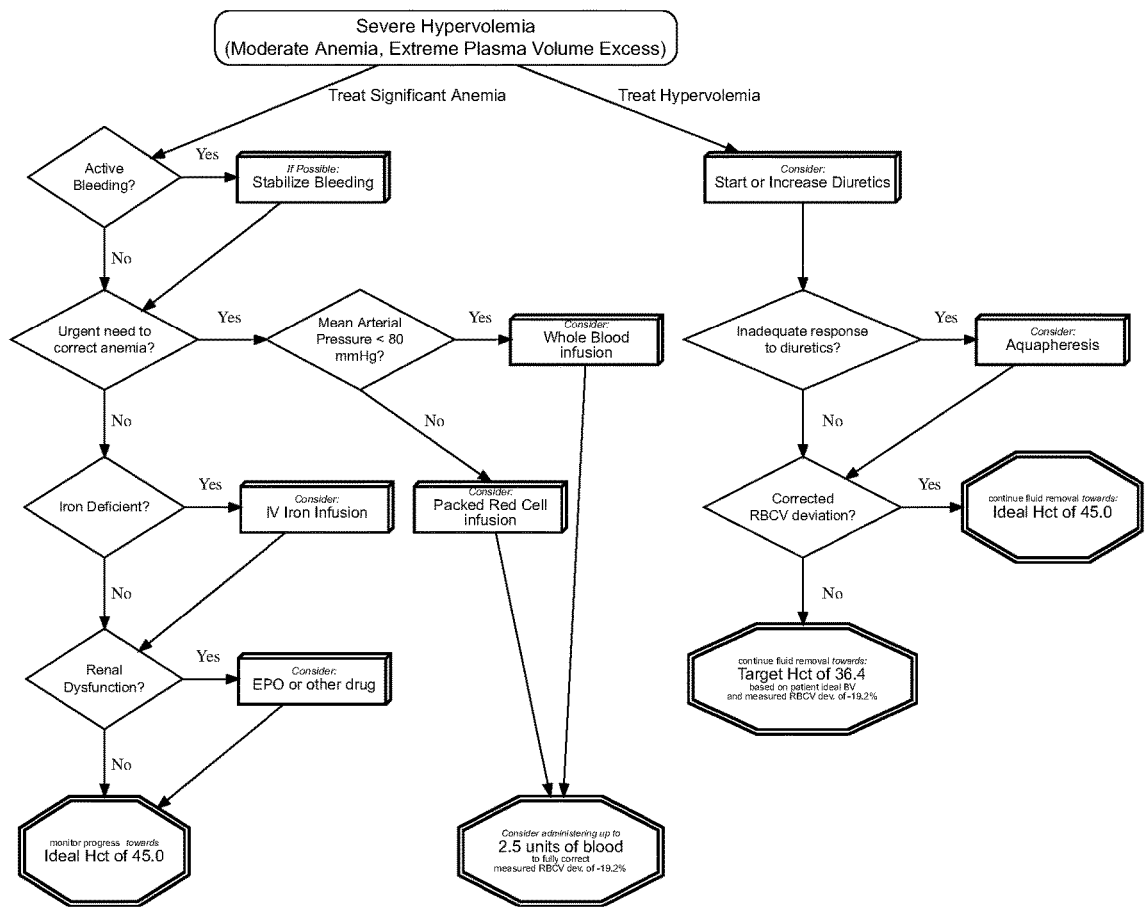

| Location | Hospital ID | Accession | Referring MD | Analyst | CC | Injectate Lot |
|---|---|---|---|---|---|---|
| *** | *** | *** | *** | *** | *** | *** |

FIGURE 17

Daxor Blood Volume Analysis Report

| Patient Name | Analyzed On | DOB | Gender | Height | Weight | Dev. from Ideal Wt. |
|---|---|---|---|---|---|---|
| *** | 2014*** | 1934*** (81 yo) | Female | 144.78 cm | 73.48 kg | +58.8% |

|  | Result | Flag | Ref. Range | Notes |
|---|---|---|---|---|
| Deviations from Ideal | | | | |
| • Total Blood Volume (% dev) | +17.6% | *H | ±11% | Moderate Hypervolemia |
| • Red Cell Volume (% dev) | -14.7% | *L | ±11% | Mild Anemia |
| • Plasma Volume (% dev) | +35.8% | *H | ±10% | Severe Plasma Volume Excess |
| Volumes | | | | |
| • Total Blood Volume (ml) | 4540 ml | *H | 3430-4280 ml | excess = 680 ml |
| • Red Cell Volume (ml) | 1180 ml | *L | 1240-1540 ml | deficit = 200 ml |
| • Plasma Volume (ml) | 3350 ml | *H | 2220-2710 ml | excess = 880 ml |
| Hct | 29 | *L | 36-44 | VERY LOW |

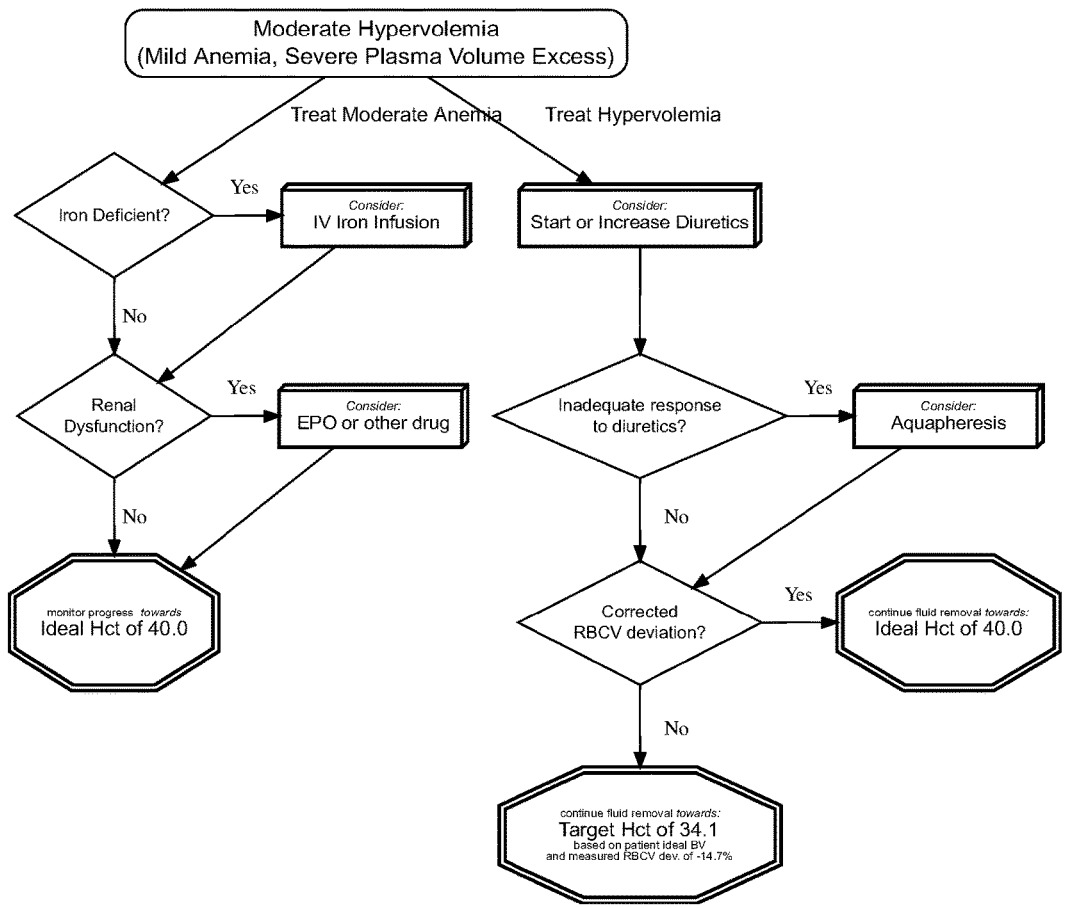

| Location | Hospital ID | Accession | Referring MD | Analyst | CC | Injectate Lot |
|---|---|---|---|---|---|---|
| *** | *** | *** | *** | *** | *** | *** |

FIGURE 18

Daxor Blood Volume Analysis Report

| Patient Name | Analyzed On | DOB | Gender | Height | Weight | Dev. from Ideal Wt. |
|---|---|---|---|---|---|---|
| *** | 2016*** | 1945*** (71 yo) | Male | 182.88 cm | 69.85 kg | -10.0% |

| | Result | Flag | Ref. Range | Notes |
|---|---|---|---|---|
| Deviations from Ideal | | | | |
| • Total Blood Volume (% dev) | +31.7% | *H | ±11% | Severe Hypervolemia |
| • Red Cell Volume (% dev) | -6.3% | | ±11% | |
| • Plasma Volume (% dev) | +57.7% | *H | ±10% | Extreme Plasma Volume Excess |
| Volumes | | | | |
| • Total Blood Volume (ml) | 6970 ml | *H | 4710-5870 ml | excess = 1680 ml |
| • Red Cell Volume (ml) | 2010 ml | | 1910-2380 ml | |
| • Plasma Volume (ml) | 4960 ml | *H | 2830-3460 ml | excess = 1820 ml |
| Hct | 32 | *L | 40.5-49 | VERY LOW |

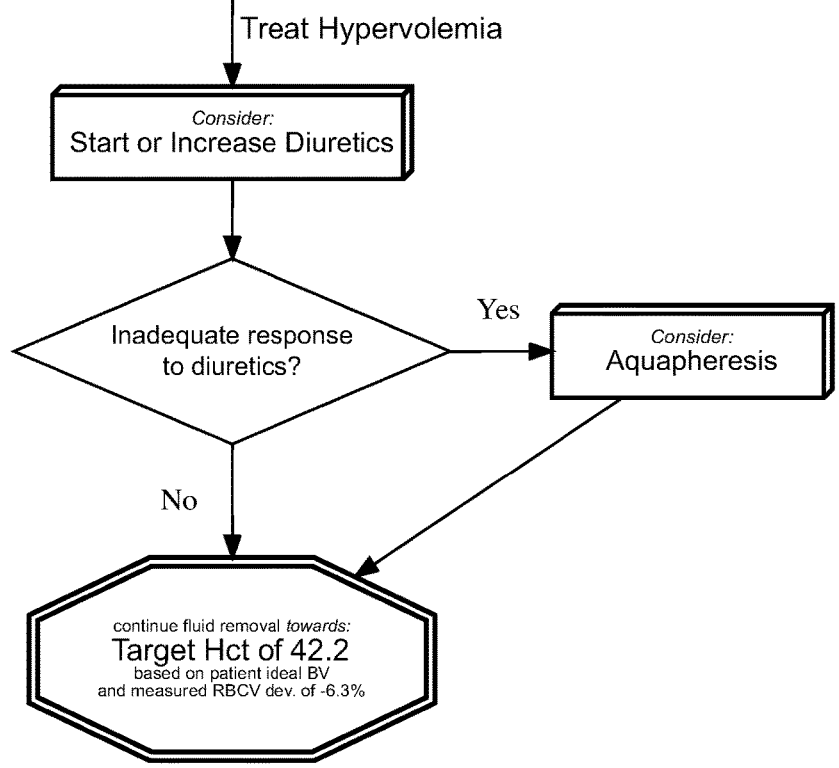

| Location | Hospital ID | Accession | Referring MD | Analyst | CC | Injectate Lot |
|---|---|---|---|---|---|---|
| *** | *** | *** | *** | *** | *** | *** |

FIGURE 19

Daxor Blood Volume Analysis Report

| Patient Name | Analyzed On | DOB | Gender | Height | Weight | Dev. from Ideal Wt. |
|---|---|---|---|---|---|---|
| *** | 2013*** | 1950*** (63 yo) | Male | 177.8 cm | 152.13 kg | +107.7% |

|  | Result | Flag | Ref. Range | Notes |
|---|---|---|---|---|
| Deviations from Ideal | | | | |
| • Total Blood Volume (% dev) | +46.6% | *H | ±11% | Extreme Hypervolemia |
| • Red Cell Volume (% dev) | +16.0% | *H | ±11% | Mild Red Cell Excess |
| • Plasma Volume (% dev) | +67.5% | *H | ±10% | Extreme Plasma Volume Excess |
| Volumes | | | | |
| • Total Blood Volume (ml) | 1.e+04 ml | *H | 6360-7940 ml | excess = 3330 ml |
| • Red Cell Volume (ml) | 3.e+03 ml | *H | 2580-3220 ml | excess = 460 ml |
| • Plasma Volume (ml) | 7.e+03 ml | *H | 3830-4680 ml | excess = 2870 ml |
| Hct | 35.6 | *L | 40.5-49 | VERY LOW |

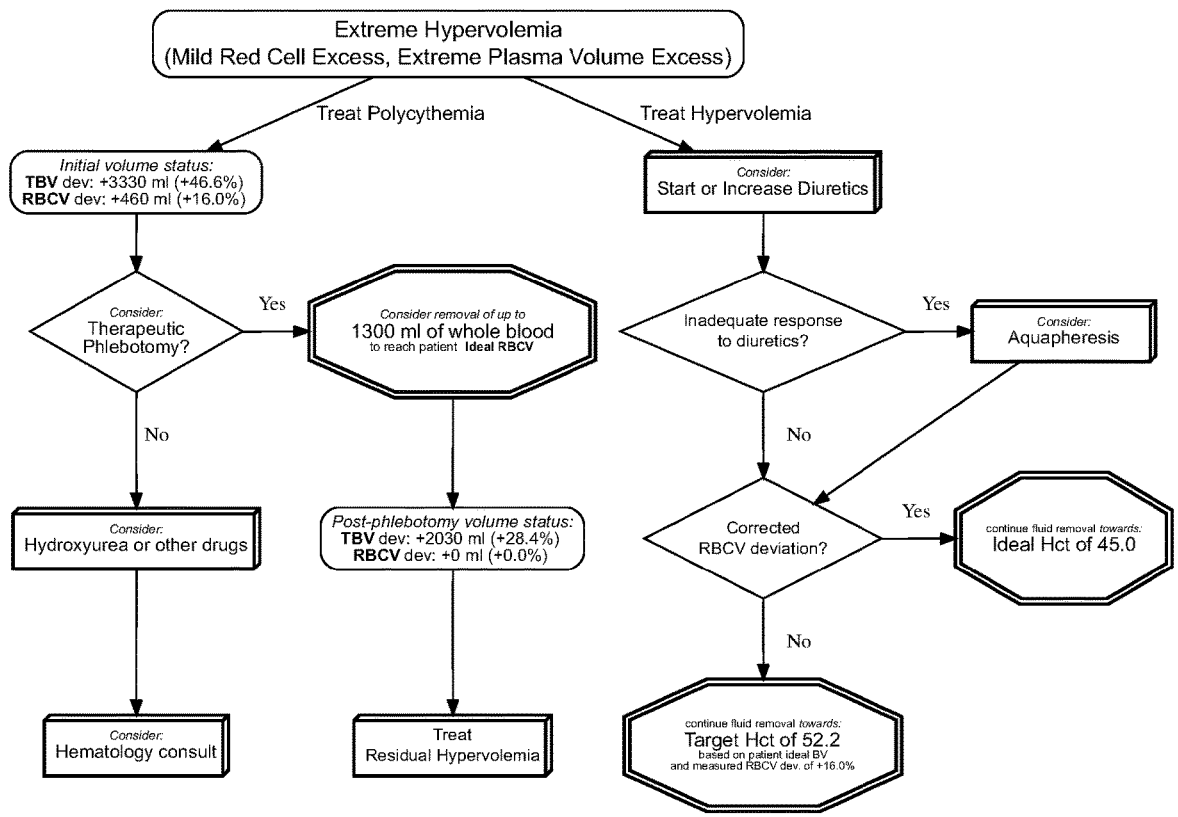

| Location | Hospital ID | Accession | Referring MD | Analyst | CC | Injectate Lot |
|---|---|---|---|---|---|---|
| *** | *** | *** | *** | *** | *** | *** |

FIGURE 20

```
Blood Volume Report:                          Analyzed on:                          Ref MD:

Patient:                                      DOB: 1943 (71 yo)                     Gender: M
                                              Height: 170.18 cm                     Weight: 78.02 kg Result    Flag    Ref. Range              Notes Total Blood Volume (% dev)  -19.4%    *L      ±11%            Moderate Hypovolemia
Red Cell Volume (% dev)     -49.8%    *L      ±11%            Extreme Anemia
Plasma Volume (% dev)       +1.4%             ±10%

Total Blood Volume (ml)     3910 ml   *L      4320-5390 ml    deficit = 940 ml
Red Cell Volume (ml)        990 ml    *L      1750-2180 ml    deficit = 980 ml
Plasma Volume (ml)          2930 ml           2600-3170 ml Hct                         28        *L      40.5-49         VERY LOW Current Volume Status: Moderate Hypovolemia
(Extreme Anemia, Normal Plasma Volume)

Guideline Interventions Report:

Handle Anemia:
  Consider IV iron infusion <-- if iron-deficient AND NOT actively bleeding
  Consider Packed Red Cell infusion <-- if severely anemic OR actively bleeding
    --> restore Ideal Red Cell Volume by correcting deficit of 980 ml with 6.1 units of packed red cells
  Consider Whole Blood Transfusion <-- if Mean Arterial Pressure < 80 mmHg, AND/OR Actively Bleeding
    --> restore Ideal Blood Volume by correcting deficit of 940 ml with 2.4 units of whole blood
  Consider EPO or other drug <-- if anemic with renal dysfunction AND/OR preserved iron stores Handle Hypovolemia:  --> Target Hct of 23 <-- if RBCV remains constant
  Consider halting or reducing diuretics <-- if patient is on diuretics
  Consider IV fluid infusion (saline and/or D5W) <-- if Mean Arterial Pressure < 80 mmHg
  Consider IV albumin infusion <-- if serum albumin < 3.0 g/dL
  Consider IV plasma replacement infusion (Ringer's Lactate, Plasma-Lyte) <-- if Mean Arterial Pressure < 80 mmHg
```

FIGURE 21

```
================================================================================
Blood Volume Report:

Patient:                              Analyzed on:                    Ref MD:

DOB: 1950 (63 yo)               Gender: M
                                      Height: 177.8 cm                Weight: 152.13 kg
================================================================================

Result      Flag      Ref. Range      Notes

Total Blood Volume (% dev)  +46.6%    *H        ±11%          Extreme Hypervolemia
Red Cell Volume (% dev)     +16.0%    *H        ±11%          Mild Red Cell Excess
Plasma Volume (% dev)       +67.5%    *H        ±10%          Extreme Plasma Volume Excess Total Blood Volume (ml)     1.e+04 ml *H        6360-7940 ml  excess = 3330 ml
Red Cell Volume (ml)        3.e+03 ml *H        2580-3220 ml  excess =  460 ml
Plasma Volume (ml)          7.e+03 ml *H        3830-4680 ml  excess = 2870 ml Hct                         35.6      *L        40.5-49       VERY LOW ================================================================================
Current Volume Status: Extreme Hypervolemia
(Mild Red Cell Excess, Extreme Plasma Volume Excess)
================================================================================

Guideline Interventions Report:
--------------------------------------------------------------------------------

Handle Polycythemia:
  Consider phlebotomy of whole blood (prior to diuresis)
    --> removal of 3330 ml of whole blood                    to achieve Ideal Blood Volume
  Consider packed RBC removal (after / without diuresis)
    --> removal of 460 ml of red cells                       to achieve Ideal Red Cell Volume
  Consider Hematology consult, Hydroxyurea / other drugs Handle Hypervolemia:  --> Target Hct of 52 <-- if RBCV remains constant
  Consider starting or increasing diuretics
  Consider aquapheresis <-- if patient is not responding adequately to diuretics ================================================================================
```

FIGURE 22

BLOOD VOLUME ANALYZER WITH GUIDANCE

CROSS-REFERENCE TO RELATED APPLICATIONS

This application claims the benefit of U.S. Provisional Patent Application No. 62/753,174, filed on Oct. 31, 2018, the contents of which are herein incorporated by reference in their entirety into the present application.

FIELD OF THE INVENTION (TECHNICAL FIELD)

The present invention relates to systems and methods for analyzing blood of a living being, and presenting guidance for medical treatment.

BACKGROUND

Various publications are referred to throughout this application, including U.S. Patent Application Publication No. US 2018/0217168 A1 (U.S. patent application Ser. No. 15/881,841). The disclosures of these publications are hereby incorporated by reference in their entirety into the subject application to more fully describe the art to which the subject invention pertains.

A blood volume analyzer (BVA) is an instrument or system capable of measuring and reporting the volume of blood of a living being. This analysis typically includes a measure of the volumes of the key blood components of red cells and plasma, using the readily measured Hematocrit (Hct), the percentage of red cells in a sample of whole blood. In many medical conditions and situations, knowledge of the blood volume status is an important or crucial component of the decision-making process for physicians. Examples include heart failure, trauma and shock, hypertension, syncope, renal failure and dialysis, etc. Published guidelines authored by various medical commissions and authorities include considerations of volume in their recommendations, but these guidelines can be difficult for caregivers to access and apply to individual patient care. This difficulty may lie in the guidelines not being easily to hand, and also more crucially in requiring the physician to do calculations to fully apply the guidelines to determine appropriate treatment for an individual patient's needs. An analyzer that incorporates guideline information can generate a report that includes specific details of blood volume intervention treatment such as amount of blood products to be used, volumes of particular blood components (whole blood, red cells) to be removed, or targets for Hct when fluids are given are removed. The combination of a guidance-equipped BVA with an instrument capable of performing blood volume interventions allows for the creation of a single instrument that can help both diagnose and treat blood volume conditions with little or no intervention.

SUMMARY OF THE INVENTION

Methods and systems are presented for analyzing the blood of a living being. A system is provided for automatically analyzing blood of a human subject, comprising a concentration counter configured to analyze one or more samples, a user interface operatively connected to the concentration counter and configured for entry and display of information, one or more processors operatively coupled to a memory and configured to execute programmed instructions stored in the memory to carry out a method comprising the steps of: gathering data, from the concentration counter, related to the concentration of a tracer within samples of blood from a human patient; calculating, by the one or more processors, a blood volume (BV), plasma volume (PV), and red cell volume (RCV) for the patient; calculating, by the one or more processors, an ideal blood volume (iBV), ideal plasma volume (iPV), and red cell volume (iRCV) for the patient based on patient descriptive data such as height, weight, and gender; calculating, by the one or more processors, treatment guidance based on the values calculated in steps (b) and (c), using protocol-derived rules stored within the system, and containing quantified patient-specific treatment information; and displaying, by the one or more processors, at the user interface, the guidance of step (d).

BRIEF SUMMARY OF EMBODIMENTS OF THE PRESENT INVENTION

In one preferred embodiment, the guidelines are integrated into the software of an automated Blood Volume Analyzer such as described in U.S. Pat. No. 5,024,231, and the guidelines are reported along with the rest of the Blood Volume Analysis report.

In another preferred embodiment, the automated analyzer uses an alternative method of measuring blood volume (rather than the indicator dilution method using a radioactive tracer such as I-131 as described in U.S. Pat. No. 5,024,231. In one preferred embodiment, this method of determining blood volume is the indicator dilution method using a light-based tracer (dye or fluorescent) rather than a radioactive tracer. In one preferred embodiment, this method of determining blood volume is the carbon monoxide rebreathing method. In one preferred embodiment, this method of determining blood volume is based on observation of real-time changes in Hct (using, e.g. a Crit-Line monitor) when changes are made to plasma volume by addition of fluids (e.g. by saline injection) or by removal of fluids (e.g. by initiating or increasing the rate of dialysis) [WO2015179401A1]

In another preferred embodiment, the guidelines are used to generate a flowchart detailing the interventions.

In another preferred embodiment, the guidelines are used to drive an interaction with a user, who supplies answers to questions contained in the guidelines; the user's answers serve to eliminate suggestions that do not apply to the particular patient.

In another preferred embodiment, the analyzer has guidelines that are/can be customized based on diagnosis/situation (e.g. heart failure, trauma, syncope, etc.).

In another preferred embodiment, the analyzer is a blood volume analyzer with volume-aware blood component measures, such as described in U.S. patent application Ser. No. 15/881,841.

In another preferred embodiment, the guidelines can be customized by the user, for example to alter thresholds, amounts, or targets for certain treatments, or to add, subtract, or rearrange possible interventions.

In another preferred embodiment, the analyzer is connected to/integrated with machinery capable of performing blood volume interventions, such as fluid addition or removal and blood product addition or removal.

In another preferred embodiment, the analyzer is capable of incorporating other patient information (entered manually or accessed via network access to patient medical records) into the patient-specific guidance it provides. This interaction occurs on a screen of the analyzer, or on a screen of a remote computing device connected to the data of the analyzer. The additional information is used to make more precise treatment suggestions In another preferred embodiment, the analyzer is capable of providing guidance for specific patient conditions beyond the scope of simple volume management, but where knowledge of volume influences treatment decisions. Such conditions include heart failure, syncope, critical care, and hypertension.

BRIEF DESCRIPTION OF THE SEVERAL VIEWS OF THE DRAWINGS

The drawings, which are incorporated herein, illustrate one or more embodiments of the present invention, thus helping to better explain one or more aspects of the one or more embodiments. As such, the drawings are not to be construed as limiting any particular aspect of any embodiment of the invention. In the drawings:

FIG. 1-20 show sample blood volume reports, as generated as part of a preferred embodiment of the invention, in which a guidance flow chart is generated along with the report of volume status.

FIG. 1 shows a guidance flowchart for a patient with significant anemia and significant hypovolemia.

FIG. 2 shows a guidance flowchart for a patient with moderate anemia and significant hypovolemia.

FIG. 3 shows a guidance flowchart for a patient with significant hypovolemia.

FIG. 4 shows a guidance flowchart for a patient with polycythemia and significant hypovolemia.

FIG. 5 shows a guidance flowchart for a patient with significant anemia and hypovolemia.

FIG. 6 shows a guidance flowchart for a patient with moderate anemia and hypovolemia.

FIG. 7 shows a guidance flowchart for a patient with hypovolemia.

FIG. 8 shows a guidance flowchart for a patient with polycythemia and hypovolemia.

FIG. 9 shows a guidance flowchart for a patient with significant anemia.

FIG. 10 shows a guidance flowchart for a patient with moderate anemia.

FIG. 11 shows a guidance flowchart for a patient with normal volume status.

FIG. 12 shows a guidance flowchart for a patient with polycythemia.

FIG. 13 shows a guidance flowchart for a patient with significant anemia and hypervolemia.

FIG. 14 shows a guidance flowchart for a patient with hypervolemia.

FIG. 15 shows a guidance flowchart for a patient with hypervolemia.

FIG. 16 shows a guidance flowchart for a patient with polycythemia.

FIG. 17 shows a guidance flowchart for a patient with significant anemia and hypervolemia.

FIG. 18 shows a guidance flowchart for a patient with moderate anemia and hypervolemia.

FIG. 19 shows a guidance flowchart for a patient with hypervolemia.

FIG. 20 shows a guidance flowchart for a patient with polycythemia and hypervolemia.

FIG. 21-22 show sample blood volume reports, as generated as part of an alternative embodiment of the invention, in which guidance is delivered in in text form (without a flow chart).

FIG. 21 shows a guidance text for a patient with Moderate Hypovolemia (Extreme Anemia, Normal Plasma Volume).

FIG. 22 shows a guidance text for a patient with Extreme Hypervolemia (Mild Red Cell Excess, Extreme Plasma Volume Excess).

DETAILED DESCRIPTION OF THE INVENTION

Figure 12:
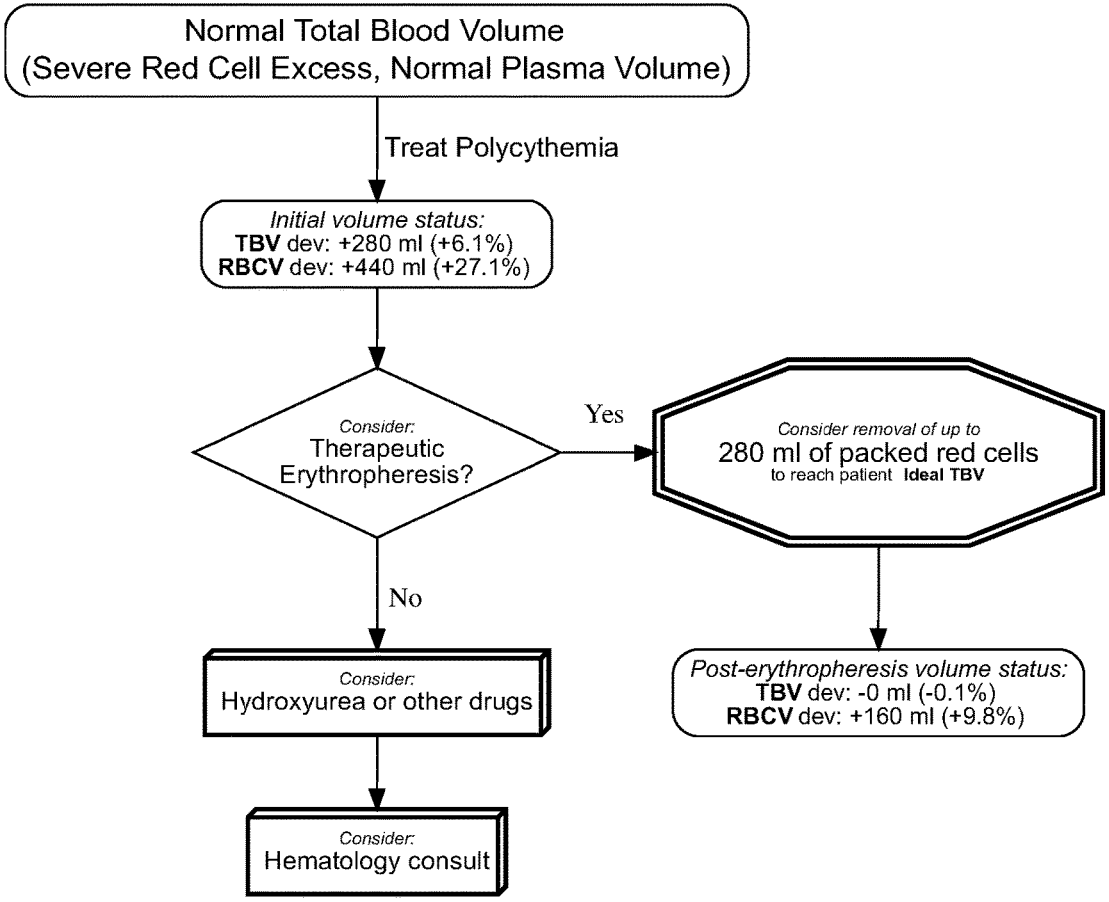

A system is provided for automatically analyzing blood of a human subject, comprising a concentration counter configured to analyze one or more samples, a user interface operatively connected to the concentration counter and configured for entry and display of information, and one or more processors operatively coupled to a memory and configured to execute programmed instructions stored in the memory to carry out a method comprising the steps of:
  a) gathering data, from the concentration counter, related to the concentration of a tracer within samples of blood from a human patient;
  b) calculating, by the one or more processors, a blood volume (BV), plasma volume (PV), and red cell volume (RCV) for the patient;
  c) calculating, by the one or more processors, an ideal blood volume (iBV), ideal plasma volume (iPV), and red cell volume (iRCV) for the patient based on patient descriptive data such as height, weight, and gender;
  d) calculating, by the one or more processors, treatment guidance based on the values calculated in steps (b) and (c), using protocol-derived rules stored within the system, and containing quantified patient-specific treatment information; and
  e) displaying, by the one or more processors, at the user interface, the guidance of step (d).

In one embodiment, step (a) comprises:
  i) injecting a tracer into the bloodstream of the human subject;
  ii) collecting one or more blood samples from the human subject over a time period after injection; and
  iii) measuring the concentration of the tracer in the various samples.

The calculations in steps (b) and (c) can be performed as follows, for example.

The overall whole body Hct (oHct) is related to the peripheral Hct by the following relationship:

$$\text{oHct} = pHct * paf \quad (1)$$

where $$paf = .9009 \quad (2).$$

This is due to the fact that blood cells are more concentrated in the peripheral circulation (from which blood samples are drawn) than the average value for the whole body; the constant paf is derived as the product 0.99*0.91, as described in U.S. Pat. No. 5,024,231, or a similar constant value. Red Cell Volume and Plasma volume are related to Blood Volume as follows:

$$BV = PV + RCV \quad (3)$$

$$RCV = BV*\text{oHct} = BV*\text{pHct}*paf \quad (4)$$

$$PV = BV*(1-\text{oHct}) = BV*(1-\text{pHct}*paf) \quad (5).$$

The Ideal Hct (iHct) is defined to be:

$$iHct \equiv \begin{cases} 0.45 \text{ for Males} \\ 0.40 \text{ for Females} \end{cases} \quad (6)$$

The Ideal Red Cell Volume (iRCV) and Ideal Plasma Volume (iPV) are calculated from the iBV. Note that the iHct is a peripheral Hct value, so the peripheral adjustment factor is required:

$$iBV = iPV + iRCV \quad (7)$$

$$iRCV = iBV*iHct*paf \quad (8)$$

$$iPV = iBV - iRCV = iBV*(1-iHct*paf) \quad (9).$$

Define the abbreviation "dev" to mean the deviation of a measured value from its respective Ideal value:

$$devBV = BV - iBV \quad (10)$$

$$devRCV = RCV - iRCV \quad (11)$$

$$devVP = PV - iPV \quad (12).$$

Define the abbreviation "edr" to mean the excess-deficit ratio of the deviation of a measured value from its Ideal value:

$$edrBV = \frac{devBV}{iBV} \quad (13)$$

$$edrRCV = \frac{devRCV}{iRCV} \quad (14)$$

$$edrPV = \frac{devPV}{iPV}. \quad (15)$$

Volume-aware metrics can now be defined that incorporate actual and ideal volume measurements into a single ratio-like (i.e. unit-less) value.

For example, the fluid corrected Hematocrit (fHct) is defined to be the peripheral Hct that would be observed, if the patient's plasma volume were adjusted so that the patient's blood volume is the Ideal Blood Volume:

$$fHct = \left(\frac{RCV}{iBV}\right) / paf. \quad (16)$$

Similarly, various other volume-aware metrics based on other treatments can be calculated, as is described in U.S. patent application Ser. No. 15/881,841 (U.S. Patent Application Publication No. US 2018/0217168 A1).

Guidance can be constructed in step (d) multiple ways. A set of rules based on the values calculated in steps (b) and (c) can be used; Table 1 below provides thresholds for such a set of rules involving calculated edrBV and edrRCV values, and the various figures in this application show guidance derived therefrom. Similarly, rules may be constructed using thresholds for various volume-aware metrics such as fHct. Guidance can also incorporate other information beyond blood volume measurements, e.g. Mean Arterial Pressure (MAP), as is shown in many figures.

In one embodiment, the tracer can be a radioactive isotope, and the counter can be a radiation counter equipped with one or more counting wells, with or without a mechanism for moving samples into counting wells. In one embodiment, the tracer can be a light-emitting (fluorescent) or light-absorbent (dye), and the counter is capable of measuring light emission or absorption either in multiple samples conveyed to the counter, or by direct measurement of circulating patient blood.

In one embodiment, where another means of measuring blood volume is employed, such as the carbon monoxide rebreathing method, or the observation of real-time changes in Hct when changes are made to plasma volume by addition of fluids or by removal of fluids.

In different embodiments, the treatment guidance is presented in one or more of textual form, flow-chart form, or interactive form, with the user answering questions pertaining to the patient, and the system presenting only guidance pertaining to the patient. The interaction can occur on the screen of a remote computing device, which is operatively connected to the data generated by the analyzer.

The protocols in step (d) can be derived from one or more published protocols relating to blood volume management. The protocols in step (d) can be customizable by the user, to include one or more of the following features:
  alteration of thresholds for consideration of a treatment,
  addition of a treatment option;
  removal of a treatment option;
  alteration of the calculation for the quantity of a treatment; and
  alteration of the order of treatment options.

One or more treatment capabilities can be connected to the system, such that quantified treatment can be administered to a patient by the system. In one embodiment, a human operator must approve a treatment before it is administered to a patient. A human operator may pre-approve a treatment based on the results of a blood volume measurement, such that it is automatically administered to a patient if the measurement-based guidance calls for it.

Treatments include, but are not limited to, addition of saline or saline-equivalent fluids, plasma or other oncotic-support fluids, or the removal of fluids via dialysis or ultrafiltration. One of the treatments can be addition of blood products such as packed red cells, whole blood, platelets, etc, or the removal of red cells via erythrocytapheresis. One of the treatments can be manipulation of a drug (stopping/starting/adjusting dosage) that is connected to a patient via IV, or via oral means.

The protocols in step (d) can be customized to include other patient information besides those in steps (1)(b) and (1)(c). The other patient information can entered by the user manually into the system. The other patient information is accessed via a network connection to the patient's medical records.

The protocols in step (d) can customized to deal with specific patient conditions beyond the scope of simple volume management, but where knowledge of volume influences treatment decisions. Such conditions can include one or more of the following: Heart Failure, Syncope, Critical Care, Hypertension, Renal Failure/Dialysis, Burns, Sepsis, Surgical Blood Loss and Hyponatremia.

Figure 23:
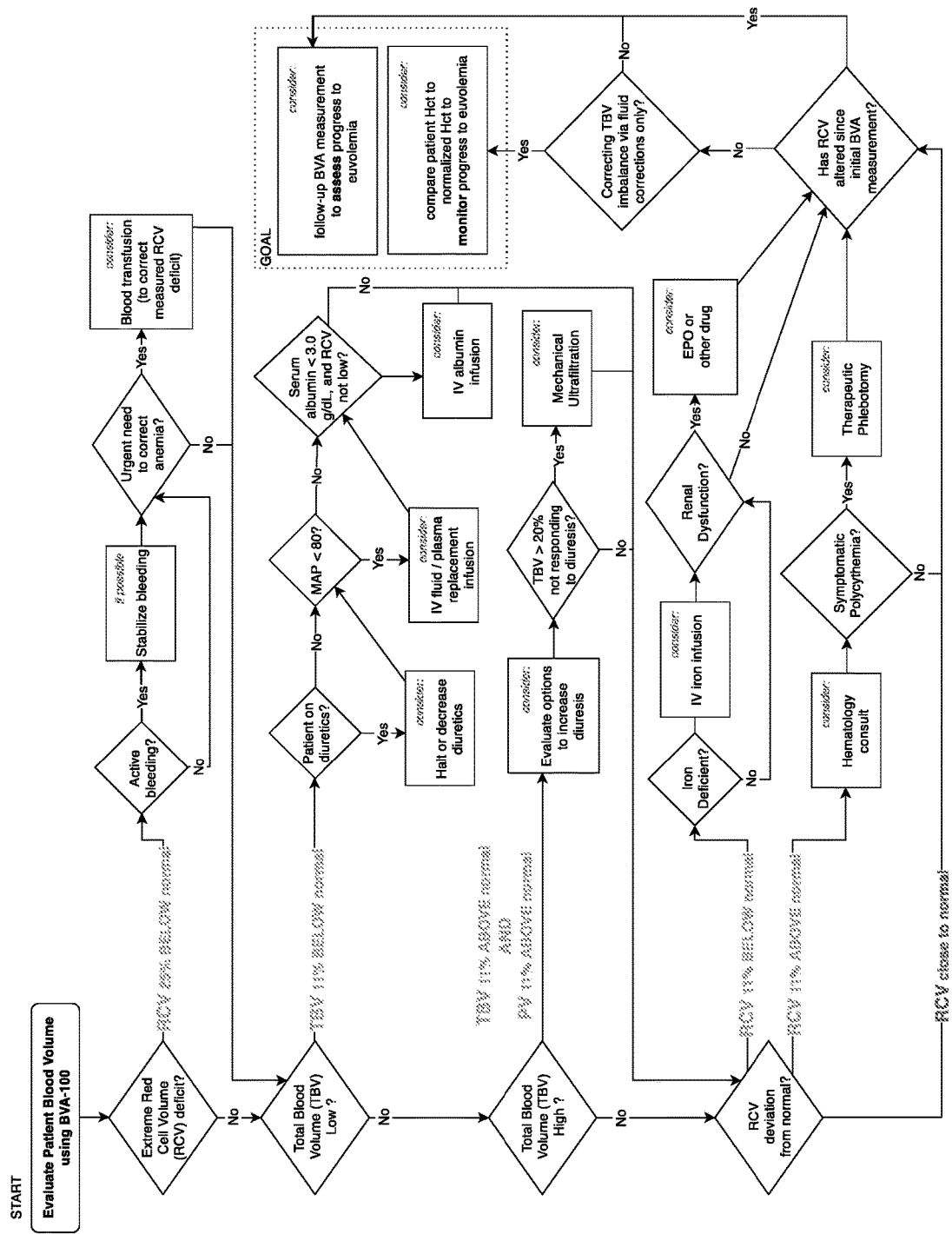
FIG. 23 shows a flowchart version of an entire protocol for a given condition (Heart Failure) with a single pathway.

Protocols for specific conditions incorporate specific additional diagnostic criteria, which together with blood volume assessment help provide differential diagnosis. For heart failure, FIG. 23 provides an example of such a protocol, which includes questions regarding a variety of patient values such as MAP, serum albumin, diuretic dosage, iron levels, etc. Various other cardiac values might also be incorporated into a more complex protocol, such as ejection fraction, right ventricular pressure values, right heart catheterization values, cardiac output, electrocardiogram (EKG) etc.

Similarly, a protocol for syncope clarifies a differential diagnosis of hypovolemia as a contributor to syncope, postural orthostatic syndrome, etc. Additional values for a syncope protocol include blood pressure measurements taken in various positions (sitting, standing, recumbent) as well as a variety of blood test values such as provided by a complete blood count (CBC).

A protocol for critical care involves information about vital signs, signs of organ hypoperfusion or organ dysfunction, nature of injury/trauma, presence of infection/antibiotic dosage, ventilation status, renal status, resuscitation and other treatments already received, etc.

A protocol for hypertension includes information about stability of blood pressure (systolic and diastolic); current medications; presence of complicating factors such as heart failure, chronic kidney disease, diabetes, etc.; presence/absence of adverse behaviors such as smoking, excessive alcohol, lack of exercise, etc.; and a variety of other medical measurements such as a CBC, EKG, lipid panel, etc.

A protocol for renal failure/dialysis includes information involving kidney function generally (such as urine output measurements, urine tests, CBC, possibly imaging/biopsy) as well as specific information related to the parameters of dialysis. In particular, knowledge of blood volume can ensure that dialysis does not result in dangerously low blood volume states, as an initial absolute blood volume can be measured, and changes in plasma volume during dialysis can be monitored, either by successive blood samples, or continuously, e.g. by a Crit-Line monitor.

A protocol for burns incorporates information about the extent and severity of burns, as well as the information mentioned above in connection with a protocol for critical care.

A protocol for sepsis incorporates information about the extent, severity, and location of infection; drug status of vasopressors/steroids/antibiotics; as well as the information mentioned above in connection with a protocol for critical care.

A protocol for surgical blood loss incorporates information about the nature and extent of surgery and anesthesia; the observed blood loss (as measured, e.g. by collected blood or bandages); whether any collected blood was returned to the patient; the presence of other compounding conditions; the patient's post-operative vs. pre-operative relative condition; and a variety of other medical measurements such as a CBC.

A protocol for hyponatremia (particularly focused on a differential diagnosis of hypotonic vs. nonhypotonic hyponatremia) includes information about the nature and duration of symptoms; current drug regimen especially vasopressors, urea, and diuretics; urinary parameters such as urinary output, urine sodium level, urine osmolarity, fractional uric acid excretion, etc.; and blood parameters including plasma copeptin concentration.

Also provided is a method of treating a patient for a condition, comprising:
  analyzing the blood of the patient with any of the systems described herein to obtain treatment guidance, or receiving treatment guidance based on this analysis; and
  administering treatment to the patient in accordance with the treatment guidance.

Such conditions can include one or more of the following: Heart Failure, Syncope, Critical Care, Hypertension, Renal Failure/Dialysis, Burns, Sepsis, Surgical Blood Loss and Hyponatremia.

Various published medical guidelines specify that patient volume status should be assessed, and that treatment should be given to restore normal volume status as part of treatment of whatever underlying or complicating condition may be present. For example, ACC/AHA/HFSA ["2017 ACC/AHA/HFSA Focused Update of the 2013 ACCF/AHA Guideline for the Management of Heart Failure: A Report of the American College of Cardiology/American Heart Association Task Force on Clinical Practice Guidelines and the Heart Failure Society of America", Clyde W. Yancy, et. al. 28 Apr. 2017 Circulation. 2017;136:e137—e161] have a Heart Failure Guideline. The European Society of Cardiology publishes guidelines that cover Acute and Chronic Heart Failure, Hypertension, Syncope, and many other conditions [https://www.escardio.org/Guidelines/Clinical-Practice-Guidelines]. Many users (hospitals, hospital groups, physicians, clinical practices, etc.) may have their own treatment guidelines, whether modified from existing guidelines or wholly unique. Such guidelines may take the form of a checklist, flowchart, or other set of instructions, or may be contained in a lengthy academic text that discusses and evaluates various treatment options. As such they may be more or less difficult to apply in a clinical setting, in particular where quantitative as well as qualitative decisions must be made for individual patients.

A report from a blood volume analyzer (such as the Daxor BVA-100, an FDA-cleared device for measuring blood volume using I-131-labelled albumin) typically includes values for Total Blood Volume (TBV), Red Cell Volume (RCV), and Plasma Volume (PV), as well as deviations from the patient ideal for those measures. Physicians armed with the information in such a report can plan interventions to correct deviations from the ideal. US Patent application publication No. US 2018/0217168 A1 (referred to above) details methods for expanding upon the information that a blood volume analyzer can provide to facilitate the planning of such interventions by expressing outcomes of treatments in terms of observed Hct values. For example, FIG. 15 of that application shows a variety of interventions that might be considered in various cases. For example, fluids might be added or removed, using the modified Hct-based quantities fHct or aHct defined therein as targets to guide treatment.

The present invention presents methods for making intervention planning substantially easier in several important ways (in various embodiments)—by providing access to relevant established, published guidelines that might not be easily to hand; by translating the volume measures into quantitative instructions for treatment directly in the metric of that treatment (e.g. units of blood products, cc of fluids, Hct target levels, etc.); by presenting guidance in a customized, easy-to-read flow chart that combines treatment questions with patient-specific treatment information; and by providing a means for automating the provision of such treatment to varying degrees.

FIGS. 1-20 show sample reports for various patients that illustrate guidance that may be issued for different volume statuses. These reports come from a preferred embodiment in which guidance is delivered in flowchart form. These figures were generated from a set of rules based on protocols based on published research [J. Strobeck, J. Feldschuh and W. Miller, "Heart Failure Outcomes With Volume-Guided Management," *JACC: Heart Failure*, vol. 6, no. 11, 2018]. The rules used thresholds defined conditions as follows:

TABLE 1

Example of thresholds for generating guidance

| Condition/Treatment | Value | Threshold (relative to Ideal) |
| --- | --- | --- |
| Hypervolemia | edrBV | >+11% |
| Aquapheresis for Hypervolemia | edrBV | >+16% |
| Anemia | edrRCV | <−11% |
| Significant Anemia | edrRCV | <−16% |
| Hypovolemia | edrBV | <−11% |
| Significant Hypovolemia | edrBV | <−15% |
| Polycythemia | edrBV | <11% |

An examination of the figures will reveal how these thresholds are used to generate the guidance. For example, FIG. 1 shows a guidance flowchart for a patient with significant anemia and significant hypovolemia, as the TBV deviation is −19.4% (which exceeds the −15% threshold) and the RCV deviation is −49.8% (which exceeds the −16% threshold). The set of treatment options (or nodes of the flowchart) is extensive. Contrast this with FIG. 6, which shows a guidance flowchart for a patient with moderate anemia and hypovolemia, as the TBV deviation is −12.1% (which exceeds the −11% but not the −15% threshold) and the RCV deviation is −14.5% (which exceeds the −11% but not the −16% threshold). FIG. 6 contains fewer treatment nodes. On the anemia treatment (left) side of FIG. 1, the node "Urgent need to treat anemia" is present, with guidance to consider blood products if mean arterial pressure is <80 mmHg. The amount of blood products to administer is calculated as 6.1 units, based on this patient's absolute RBCV deficit, and the known amount of red blood cells in a unit of blood. On the hypervolemia (right) side of FIG. 1, additional nodes are present for the consideration of treatments "IV plasma replacement infusion" and "IV albumin infusion" which are absent in FIG. 6. Target Hct values are specified in the various figures in accordance with calculations shown in application Ser. No. 15/881,841.

In the example figures, interventions are indicated with rectangular nodes, questions with diamond-shaped nodes, and targets and quantified treatments with octagonal nodes. Charts are generated with Graphviz DOT software. One skilled in the art would recognize other software tools to generate flowcharts programmatically, be able to integrate such tools into a software system, as well as envision alternative graphical formats.

FIGS. 21 and 22 are generated with similar rules, and show another embodiment, in which treatment guidelines are given in text form, with questions and quantitative treatment amounts. One skilled in the art would see how, based on these illustrative examples and descriptions, additional treatments and thresholds could be programmed into the system.

FIG. 23 shows a plan of guidance, in which a single path of treatment is presented to deal with derangements in both red cell volume and total blood volume for a particular condition, in this case heart failure. This diagram shows a full range of possible deviations (RCV high, RCV low, TBV high, TBV low). The advantage of a single treatment path is that it helps to specify the order in which treatment options should be considered. This chart is not customized for a single patient's results, but instead shows the full range of options that can appear. It is helpful for demonstrating the thresholds and options that are included in a given treatment protocol (for example when the protocol is being specified and agreed upon by appropriate medical decision makers).

Figure 24:
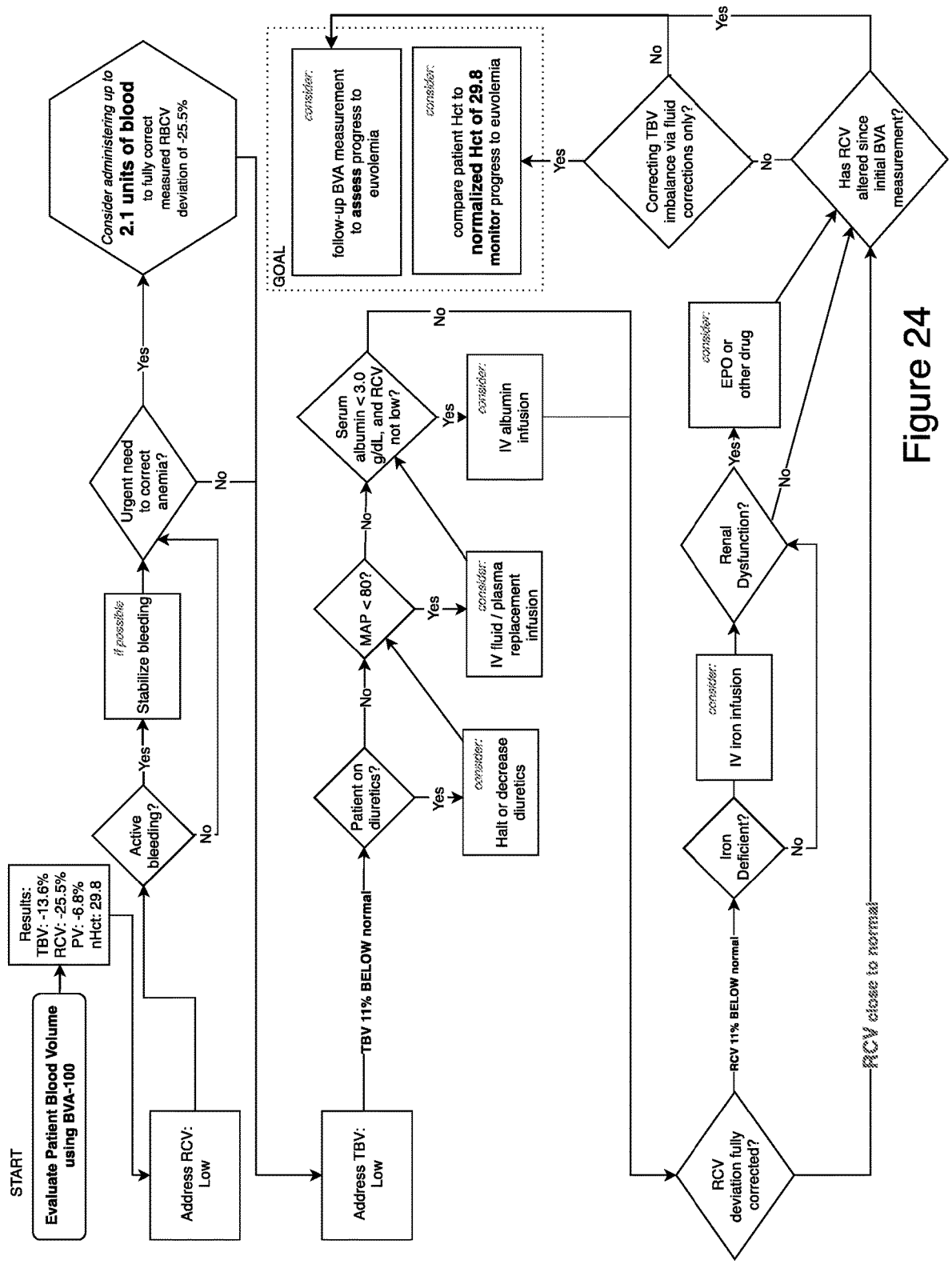
FIG. 24 shows a individualized flowchart for a given patient, using the single-pathway protocol of FIG. 23.

FIG. 24 shows an example of a customized guidance flowchart derived from the protocol shown in FIG. 23. This chart is for a patient with a RCV deviation of −25.5% and a TBV deviation of −13.6% (this is the same patient as in FIG. 5). FIG. 24 shows a single pathway of treatment options, in contrast to the two separate pathways in FIG. 5 (for treating anemia and hypovolemia). In contrast to FIG. 23, FIG. 24 provides patient-specific quantitative information: quantifying 2.1 units of blood as a possible intervention (based on dividing the RCV deviation expressed as a volume by a constant defining the red cell volume of a "unit" of blood, e.g. 160 ml/unit), and specifying the Hct value of 29.8 as a basis of comparison to monitor progress to euvolemia. (Note that the target of 29.8 is only used if the RCV deficit is uncorrected—in this case, the treatment course is aimed at correcting the TBV deficit only, and the resulting treatment would be an addition of fluids, which would have the effect of hemodilution, thus lowering the observed pHct from 34.5 to 29.8.)

Figure 25:
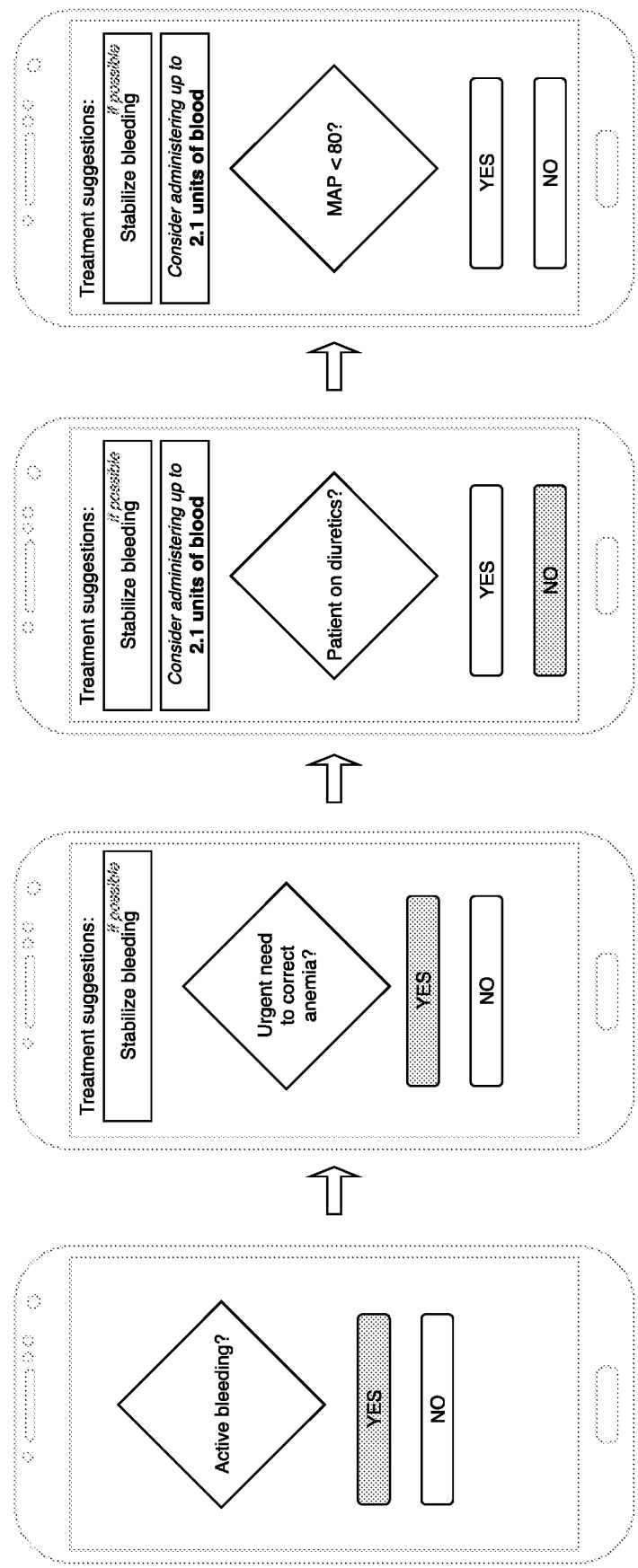
FIG. 25 shows a series of screen images, depicting the interactive generation of guidance by a user interacting with a screen.

The flowcharts displayed in the figures can also be used as the basis for an interactive presentation of the guidance, in which a user is presented with the questions contained in the diamond-shaped nodes, and the user's answers to the questions are used to determine the treatment options that are presented to the user. Such an interactive presentation of the guidance could be implemented on the screen of the analyzer itself, or on the screen of another computing device (such a laptop or phone) which has a data connection to the analyzer or a database repository of results from the analyzer. FIG. 25 shows an example of an interaction taking place on the screen of a device such as a phone, using the same patient from FIG. 24. A user answers questions (by tapping on the "Yes" or "No" buttons) and the relevant treatment suggestions appear on the screen. As the user moves through the questions (the diamond-shaped nodes in FIG. 24), only the relevant treatment suggestions are displayed, and inapplicable ones are never shown to the user. For example, in the left-most screen in FIG. 25, the user answers "Yes" to the question "Active bleeding?". As a result, in the second screen, the treatment suggestion "If possible Stabilize bleeding" appears and remains through succeeding steps. Similarly, the user answering "Yes" to "Urgent need to correct anemia" results in the display of the suggestion "Consider administering 2.1 units of blood". In contrast, after the user answers "No" to the question "Patient on diuretics?" the treatment suggestion "Halt or decrease diuretics" does not appear, and the interaction moves on to the next question "MAP <80?". The process continues beyond the screens depicted in FIG. 25 until all the relevant questions have been answered. One skilled in the art would recognize that there are many programmatic and visual forms that this interaction could take, based on various computing devices and screens. One skilled in the art would also recognize that there are many further actions that the user and/or system could take once the treatment suggestions are created, such as printing the suggestions out, appending them to the patient's BVA analysis report, appending them to the patient's electronic medical record, storing them in the device database, sharing them with others via electronic messaging, etc.

Figure 26:
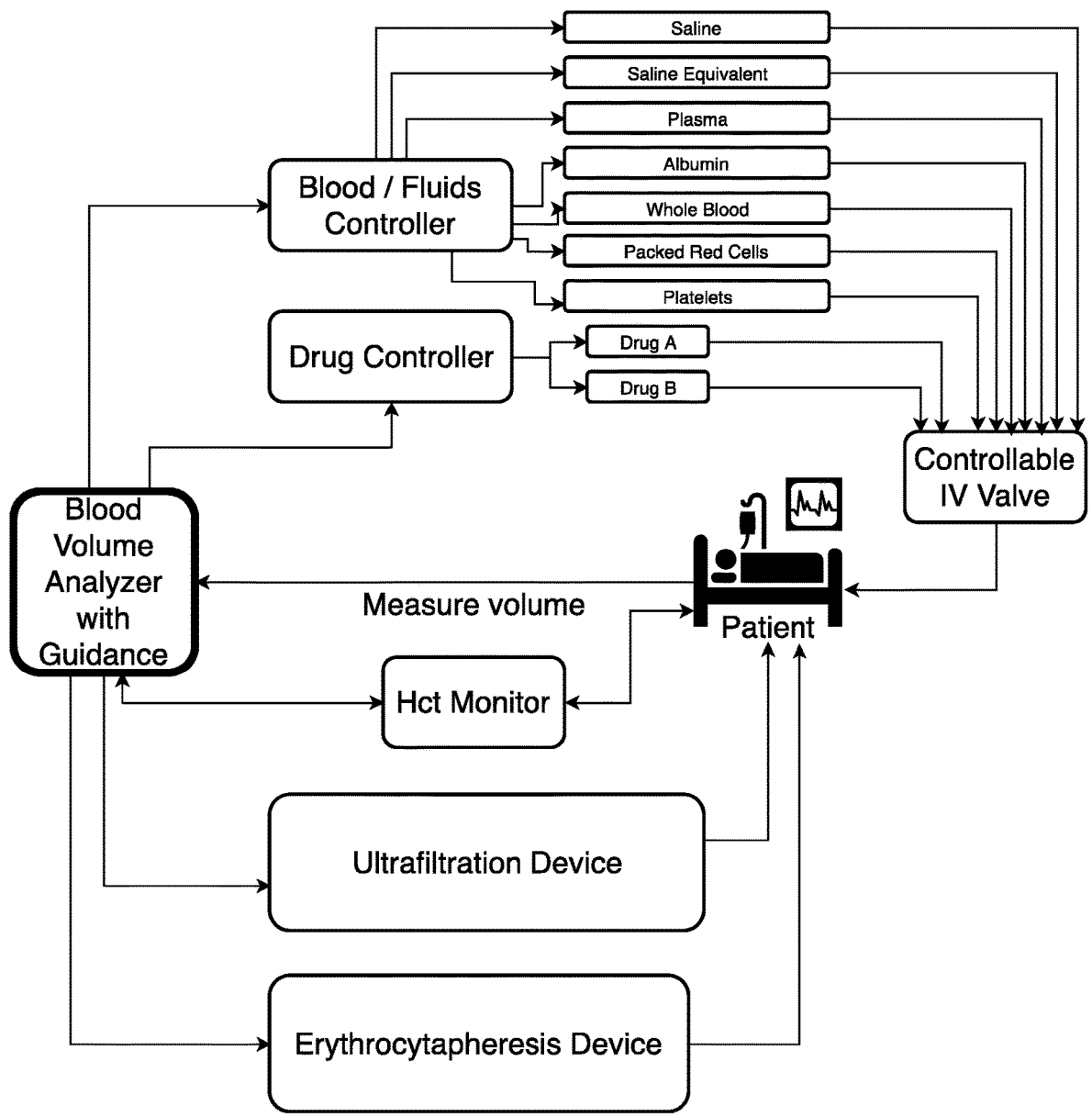
FIG. 26 shows a schematic of an integrated blood volume analyzer and volume correction instrument. This instrument is capable of performing a blood volume measurement, and administering guideline-based volume correction treatment while monitoring patient Hct. Such treatment could consist of addition or removal of fluids, addition or removal of red blood cells or other blood products, and administering other drugs or treatments.

FIG. 26 shows a schematic of a preferred embodiment of an integrated blood volume analyzer and volume correction system. This system is capable of performing a blood volume measurement and administering guideline-based volume correction treatment while monitoring patient Hct. Such treatment could consist of addition or removal of fluids, addition or removal of red blood cells or other blood products, and administering other drugs or treatments. The Blood Volume Analyzer with Guidance first performs a measurement of the patient's volume status. Based on the guidance report generated, various fluids and blood products (such as saline, whole blood, etc.) may be administered, by connecting such products to a controllable IV valve that is connected to the patient. Blood products would need to be compatible with the patient's blood type and other factors. Other drugs (Drug A, Drug B, etc) could also be controlled in a similar manner, either through the IV valve or through other means of administration (e.g. oral), not depicted. The attached Hct monitor (such as a Crit-Line or similar device) measures peripheral Hct continuously, allowing continuous comparison of pHct with fHct, aHct, rHct etc. as specified in application 15881841. Attached Ultrafiltration and Erythrocytapheresis devices may be controlled by the Blood Volume Analyzer to operate until pHct reaches a certain target (fHct, aHct, rHct) etc.

The systems and methods of the present invention represent an improvement of current systems and methods for analyzing blood of a patient, and for presenting guidance for medical treatment of the subject.

One skilled in the art will recognize how a system with a subset of these connections might function, as well as how other products and controllers could be similarly connected. For example, other monitors of vital signs beyond Hct could be integrated, connections could be made to patient records to receive other information, alerts could be provided to medical staff to authorize/approve some or all treatments prior to administration, etc.

What is claimed is:

1. A method of treating a patient for correction of blood volume, comprising:
   A) receiving a treatment recommendation based on an analysis of the patient's blood, wherein the analysis was conducted using a system for automatically analyzing blood of a human patient and for providing a quantified patient-individualized treatment for correction of blood volume in patient conditions where knowledge of patient blood volume influences treatment decisions, the system comprising a concentration counter configured to analyze one or more samples, a user interface operatively connected to the concentration counter and configured for entry and display of information, and one or more processors operatively coupled to a memory and configured to execute programmed instructions stored in the memory to carry out a method comprising the steps of:
   (a) the concentration counter collecting at least one tracer count related to the concentration of a tracer within samples of blood from the human patient;
   (b) the one or more processors calculating from the tracer count a blood volume (BV), plasma volume (PV), and red cell volume (RCV) for the patient;
   (c) inputting patient descriptive data to the one or more processors;
   (d) the one or more processors calculating from the patient descriptive data an ideal blood volume (iBV), ideal plasma volume (iPV), and ideal red cell volume (iRCV) for the patient;
   (e) one or more processors providing a quantified patient-individualized treatment recommendation based on the patient's blood volume as expressed by the values calculated in steps (b) and (d), and protocol-derived rules stored within the system; and
   (f) displaying, by the one or more processors, at the user interface, the treatment recommendation of step (e),
   wherein the treatment recommendation is one or more of:
   administration of saline or saline-equivalent fluids, plasma or oncotic-support fluids to a patient with low BV,
   removal of fluids via dialysis or ultrafiltration from a patient with high BV,
   administration of packed red blood cells, whole blood, or platelets to a patient with low RCV,
   removal of red blood cells from a patient with high RCV,
   removal of whole blood from a patient with high RCV via therapeutic phlebotomy,
   stopping or lowering the dose of a diuretic drug for a patient with low BV, and
   administering or increasing the dose of a diuretic drug for a patient with high BV; and
   B) administering treatment to the patient in accordance with the treatment recommendation;
   wherein the treatment is one or more of:
   administering saline or saline-equivalent fluids, plasma or oncotic-support fluids to a patient with low BV,
   removing fluids via dialysis or ultrafiltration from a patient with high BV,
   administering packed red blood cells, whole blood, or platelets to a patient with low RCV,
   removing red blood cells from a patient with high RCV via erythrocytapheresis,
   removing whole blood from a patient with high RCV patient via therapeutic phlebotomy,
   stopping or lowering the dose of a diuretic drug for a patient with low BV, and
   administering or increasing the dose of a diuretic drug for a patient with high BV.

2. The method of claim 1, where step (a) comprises:
   i. injecting a tracer into the bloodstream of the human patient;
   ii. collecting one or more blood samples from the human patient over a time period after injection; and
   iii. measuring the concentration of the tracer in the various samples.

3. The method of claim 2, where the tracer is a radioactive isotope, and the counter is a radiation counter equipped with one or more counting wells, with or without a mechanism for moving samples into counting wells.

4. The method of claim 1, wherein step (a) comprises:
   i. injecting a light-emitting fluorescent or light-absorbent dye into the blood stream of the human patient, and
   ii. measuring light emission or absorption either in multiple samples conveyed to the counter, or by a concentration counter capable of direct measurement of circulating patient blood.

5. The method of claim 1, where an additional means of measuring blood volume is employed to obtain values specified in steps (b) and (d), wherein the additional means is a carbon monoxide rebreathing method or observation of real-time changes in Hct when changes are made to plasma volume by addition of fluids or by removal of fluids.

6. The method of claim 1, where the treatment recommendation is presented in textual or flow-chart form.

7. The method of claim 1, where the treatment is presented in interactive form, with the user answering questions pertaining to the patient, and the system presenting only recommendations pertaining to the patient.

8. The method of claim 7, where the interaction occurs using a remote computing device, which is programmed to perform steps (e) and (f) using values calculated in steps (b) and (d).

9. The method of claim 1, where the protocols in step (e) are derived from one or more published protocols relating to blood volume management.

10. The method of claim 1, where the protocols in step (e) are customizable by the user, to include one or more of the following features:
   a. alteration of thresholds for consideration of a treatment,
   b. addition of a treatment option,
   c. removal of a treatment option,
   d. alteration of the calculation for the quantity of a treatment, and
   e. alteration of the order of treatment options.

11. The method of claim 1, where the patient has one or more of the following conditions:
   (a) heart failure,
   (b) syncope,
   (c) critical care,
   (d) hypertension,
   (e) renal failure/dialysis,
   (f) burns,
   (g) sepsis,
   (h) surgical blood loss,
   (i) hyponatremia.

12. A system for automatically analyzing blood of a human patient and for providing a quantified patient-individualized treatment for correction of blood volume in patient conditions where knowledge of patient blood volume influences treatment decisions, the system comprising a concentration counter configured to analyze one or more samples, a user interface operatively connected to the concentration counter and configured for entry and display of information, a volume correction subsystem, and one or more processors operatively coupled to a memory and configured to execute programmed instructions stored in the memory to carry out a method comprising the steps of:
   (a) the concentration counter collecting at least one tracer count related to the concentration of a tracer within samples of blood from the human patient;
   (b) the one or more processors calculating from the tracer count a blood volume (BV), plasma volume (PV), and red cell volume (RCV) for the patient;
   (c) inputting patient descriptive data to the one or more processors;
   (d) the one or more processors calculating from the patient descriptive data an ideal blood volume (iBV), ideal plasma volume (iPV), and ideal red cell volume (iRCV) for the patient;
   (e) one or more processors providing a quantified patient-individualized treatment recommendation based on the patient's blood volume as expressed by the values calculated in steps (b) and (d), and protocol-derived rules stored within the system;
   (f) displaying, by the one or more processors, at the user interface, the treatment recommendation of step (e), wherein the treatment recommendation is one or more of:
      administration of saline or saline-equivalent fluids, plasma or oncotic-support fluids to a patient with low BV,
      removal of fluids from the patient via dialysis or ultrafiltration from a patient with high BV,
      administration of a blood product such as packed red blood cells, whole blood, or platelets to a patient with low RCV,
      removal of red blood cells from a patient with high RCV via erythrocytapheresis,
      removal of whole blood from a patient with high RCV via therapeutic phlebotomy,
      stopping or lowering the dose of a diuretic drug for a patient with low BV, and
      administering or increasing the dose of a diuretic drug for a patient with high BV; and
   (g) administering treatment to the patient in accordance with the treatment recommendation via the volume correction subsystem, wherein the treatment is one or more of:
      administering saline or saline-equivalent fluids, plasma or oncotic-support fluids to a patient with low BV,
      removing fluids via dialysis or ultrafiltration from a patient with high BV,
      administering a blood product such as packed red blood cells, whole blood, or platelets to a patient with low RCV,
      removing red blood cells from a patient with high RCV via erythrocytapheresis,
      removing whole blood from a patient with high RCV via therapeutic phlebotomy,
      stopping or lowering the dose of a diuretic drug for a patient with low BV, and
      administering or increasing the dose of a diuretic drug for a patient with high BV.

13. The system of claim 12, where the volume correction subsystem includes one or more of the following components connected to the patient:
   (a) a controllable IV valve connected to saline or saline-equivalent fluids, plasma or oncotic-support fluids,
   (b) a controllable IV valve connected to whole blood or packed red cells,
   (c) a controllable IV valve connected to diuretic drugs,
   (d) an ultrafiltration or dialysis device,
   (e) an erythrocytapheresis device.

14. The system of claim 12, where a continuous hematocrit monitoring device is connected to the one or more processors, and the updated hematocrit value is used in step (b) to provide an updated treatment recommendation and treatment administration in steps (e)-(g).

15. The system of claim 12, where a human operator must approve a treatment before it is administered to the patient.

16. The system of claim 12, where a human operator pre-approves a treatment based on the results of a blood volume measurement, such that it is automatically administered to the patient if the measurement-based recommendation calls for it.

17. The system of claim 12, where the protocols in step (e) are customized to include other information from the patient besides those in steps (b) and (c).

18. The system of claim 17, where the other information from the patient is entered by the user manually into the system or is accessed via a network connection to medical records for the patient.

19. The system of claim 12, where the protocols in step (e) are customized to deal with specific patient conditions beyond the scope of simple volume management, but where treatment decisions include an aim to correct blood volume.

20. The system of claim 19, where the condition is one or more of the following conditions:
   a. heart failure,
   b. syncope,
   c. critical care,
   d. hypertension,
   e. renal failure/dialysis,
   f. burns,
   g. sepsis,
   h. surgical blood loss,
   i. hyponatremia.

\* \* \* \* \*